(12) United States Patent
Foo et al.

(10) Patent No.: US 11,284,656 B2
(45) Date of Patent: Mar. 29, 2022

(54) ELASTOMERIC GLOVES AND METHODS FOR THEIR PRODUCTION

(71) Applicant: SKINPROTECT CORPORATION SDN BHD, Selangor (MY)

(72) Inventors: Khon Pu Foo, Selangor (MY); Kumaresan Prabhakaran, Selangor (MY)

(73) Assignee: SKINPROTECT CORPORATION SDN BHD, Selangor (MY)

( * ) Notice: Subject to any disclaimer, the term of this patent is extended or adjusted under 35 U.S.C. 154(b) by 563 days.

(21) Appl. No.: 16/015,786

(22) Filed: Jun. 22, 2018

(65) Prior Publication Data

US 2019/0029342 A1 Jan. 31, 2019

Related U.S. Application Data

(60) Provisional application No. 62/536,887, filed on Jul. 25, 2017.

(30) Foreign Application Priority Data

Jul. 25, 2017 (AU) ................................ 2017902922

(51) Int. Cl.
*A41D 19/00* (2006.01)
*B29D 99/00* (2010.01)
(Continued)

(52) U.S. Cl.
CPC ..... *A41D 19/0082* (2013.01); *A41D 19/0058* (2013.01); *A41D 19/04* (2013.01);
(Continued)

(58) Field of Classification Search
CPC ............ A41D 19/0055; A41D 19/0062; A41D 19/0082; A41D 19/0058; C08F 236/12
See application file for complete search history.

(56) References Cited

U.S. PATENT DOCUMENTS 2,662,874 A 12/1953 Brown et al.
2,859,193 A 11/1958 Kowalewski
(Continued)

FOREIGN PATENT DOCUMENTS

AU 2015200988 B2 3/2015
CN 101028742 A 9/2007
(Continued)

OTHER PUBLICATIONS

Datta, R.N., "Rubber Curing Systems", Rapra Review Reports, Report 144, vol. 12, No. 12 (2002) (in English; 157 pages).
(Continued)

*Primary Examiner* — Tajash D Patel
(74) *Attorney, Agent, or Firm* — Westerman, Hattori, Daniels and Adrian, LLP

(57) ABSTRACT

The present application provides low thickness synthetic elastomeric gloves, comprising (a) a thickness at the palm of less than 0.050 mm; (a) a modulus at 500% above 6.5 MPa; and/or (c) an elongation at break below 700%. Also provided is a method for the manufacture of such gloves involving dipping a glove-shaped former into an elastomeric film-forming composition; and curing the elastomeric film-forming composition on the former so as to produce the synthetic elastomeric glove. Corresponding low thickness finger cots are also described, as are formers suitable for the preparation of such gloves.

32 Claims, 4 Drawing Sheets

(51) Int. Cl.
  *B29C 41/14* (2006.01)
  *A61B 42/10* (2016.01)
  *A61B 42/00* (2016.01)
  *A41D 19/04* (2006.01)
  *C08C 1/02* (2006.01)
  *C08F 236/12* (2006.01)
  *A61B 17/00* (2006.01)
  *B29L 31/48* (2006.01)

(52) U.S. Cl.
  CPC .............. *A61B 42/00* (2016.02); *A61B 42/10* (2016.02); *B29C 41/14* (2013.01); *B29D 99/0067* (2013.01); *C08C 1/02* (2013.01); *C08F 236/12* (2013.01); *A41D 19/0044* (2013.01); *A41D 2400/44* (2013.01); *A41D 2400/70* (2013.01); *A41D 2500/54* (2013.01); *A61B 2017/00526* (2013.01); *B29L 2031/4864* (2013.01); *C08F 2810/20* (2013.01); *Y10S 428/923* (2013.01); *Y10S 428/925* (2013.01); *Y10T 428/24* (2015.01); *Y10T 428/24942* (2015.01); *Y10T 428/26* (2015.01); *Y10T 428/298* (2015.01)

(56) References Cited

U.S. PATENT DOCUMENTS

| | | | |
|---|---|---|---|
| 2,868,754 | A | 1/1959 | Eilbeck et al. |
| 3,403,136 | A | 9/1968 | Baker |
| 3,976,723 | A | 8/1976 | Williams et al. |
| 4,329,312 | A | 5/1982 | Ganz |
| 4,525,517 | A | 6/1985 | Sato |
| 5,014,362 | A | 5/1991 | Tillotson et al. |
| 5,559,263 | A | 9/1996 | Smith |
| 5,993,923 | A | 11/1999 | Lee |
| 6,000,061 | A | 12/1999 | Taneja et al. |
| 6,081,928 | A | 7/2000 | Bourne |
| 6,492,446 | B1 | 12/2002 | Kajiwara et al. |
| 6,828,387 | B2 | 12/2004 | Wang et al. |
| 7,356,852 | B2 | 4/2008 | Thai |
| 7,721,354 | B2 | 5/2010 | Yu et al. |
| 8,273,810 | B2 | 9/2012 | Wang et al. |
| 9,085,100 | B2 | 7/2015 | Foo |
| 2006/0253956 | A1* | 11/2006 | Lipinski ............... C08L 9/02 2/168 |
| 2008/0139723 | A1 | 6/2008 | Foo |
| 2008/0227913 | A1 | 9/2008 | Koide |
| 2008/0306200 | A1 | 12/2008 | Chen et al. |
| 2010/0257657 | A1 | 10/2010 | Hamann et al. |
| 2012/0204321 | A1 | 8/2012 | Connelly et al. |
| 2015/0218352 | A1 | 8/2015 | Enomoto et al. |
| 2015/0272241 | A1* | 10/2015 | Lucas ............... C08L 7/00 2/167 |
| 2016/0194494 | A1 | 7/2016 | Foo et al. |
| 2017/0099889 | A1 | 4/2017 | Liou |
| 2017/0137584 | A1 | 5/2017 | Tung et al. |
| 2018/0332910 | A1* | 11/2018 | Modha ............... B29C 41/22 |
| 2020/0170320 | A1* | 6/2020 | Robert ............... A41D 19/043 |

FOREIGN PATENT DOCUMENTS

| | | |
|---|---|---|
| CN | 101175809 A | 5/2008 |
| GB | 851045 A | 10/1960 |
| GB | 862372 A | 3/1961 |
| WO | 2004044037 A1 | 5/2004 |
| WO | 2009134702 A1 | 11/2009 |
| WO | 2010023634 A2 | 3/2010 |
| WO | 2015006806 A1 | 1/2015 |
| WO | 2015006807 A1 | 1/2015 |
| WO | 2015006808 A1 | 1/2015 |
| WO | 2016058029 A1 | 4/2016 |
| WO | 2016072835 A1 | 5/2016 |
| WO | 2017087797 A1 | 5/2017 |
| WO | 2017116227 A1 | 7/2017 |

OTHER PUBLICATIONS

Joseph, Rani, "Practical Guide to Latex Technology", Smithers Rapra Technology, Ltd. (2013) (in English; 121 pages).
Klingender, Robert C., "Handbook of Specialty Elastomers", published by CRC Press, Taylor & Francis Group, (2008) (in English; 572 pages).
Examination Report No. 2, dated Jul. 11, 2019, issued in corresponding Australian Patent Application No. 2018204560 (6 pages; in English).
Examination Report No. 2 (Reissue), dated Jul. 12, 2019, issued in corresponding Australian Patent Application No. 2018204560(6 pages; in English).
Office Action dated Aug. 13, 2021, issued in counterpart Indonesian Application No. P00202001406 (w/ English translation; 9 pages).
Office Action dated Nov. 1, 2021, issued in counterpart Chinese Application No. 201880005060.9 (w/ English machine translation; 26 pages).

* cited by examiner

ELASTOMERIC GLOVES AND METHODS FOR THEIR PRODUCTION

RELATED APPLICATIONS

This application claims priority from U.S. provisional patent application No. 62/536,887 and Australian provisional patent application no. 2017902922, each filed on 25 Jul. 2017, the entirety of which are incorporated herein by reference.

FIELD

The present application relates to elastomeric gloves and methods for their production. The present application relates in particular to low thickness or low weight elastomeric gloves. Also described herein are formers suitable for use in the production of such gloves.

BACKGROUND

Thin film, disposable elastomeric gloves are used extensively in medical or dental environments, and in other situations where barrier protection for the hands is required. For those who use such gloves repeatedly, it is desirable for the glove to be as thin as possible, while still having good barrier properties, elasticity, and stretchability, so as to maximise the touch sensation that is experienced through the gloves. Thin film elastomeric gloves also have the potential to replace the use of polyvinylchloride (PVC) gloves in the food handling/food service industry. PVC gloves contain plasticisers which may be toxic to human health, so thin film gloves based on elastomers such as nitrile rubber and the like which are free of plasticisers, rather than PVC, are also of interest to such industries. In addition, in some less developed countries, there have been reports that the use of disposable gloves for hygiene purposes is banned due to the high cost and lack of budget for such products. An alternative product that is of lower cost, due to lower material input, would be of potential interest in such countries. Furthermore, it would be of interest to be able to produce gloves using less material (i.e. less polymer material), less chemicals (i.e. other reagents), less energy and with the production of a reduced volume of waste following disposal of the used gloves. Such products would better conform to green technologies.

While it is desirable to produce extremely thin, low weight gloves, in practice the technology has not been available to achieve this. In printed publications there may be reference to gloves having certain broad-ranging properties and thicknesses (or weight), but without the technology being available to enable such thin gloves to be produced with acceptable properties, such disclosures may be read with skepticism. It is particularly difficult to achieve this with synthetic elastomers, which are used in place of natural rubber. The use of natural rubber is not desirable since it is associated with a potential allergen that causes Type I allergy.

It is an object of the present invention to provide new elastomeric articles that provide the desired features described above, or to at least provide an alternative glove to those currently available.

SUMMARY

According to the present invention, there is provided a synthetic elastomeric glove with:
(a) a thickness at the palm of less than 0.05 mm;
(b) a modulus at 500% above 6.5 MPa; and/or
(c) an elongation at break below 700%.

According to the present invention there is also provided a method of manufacturing the synthetic elastomeric glove described above comprising:
dipping a glove-shaped former into an elastomeric film-forming composition;
curing the elastomeric film-forming composition on the former so as to produce the synthetic elastomeric glove.

The applicant has, for the first time, achieved the production of ultra-thin, low weight gloves.

Gloves are formed from latex compositions (in this case, synthetic latex compositions), which comprise a synthetic polymer and a cross-linking agent. The applicant has produced the new ultra-thin gloves using a range of cross-linking agents in the latex composition. In some embodiments, the cross-linking agent comprises a multimetal oxide of a multivalent metal, a hydroxide of a multivalent metal or a salt of a multivalent metal. This cross-linking agent is suitably pre-formulated into a cross-linking composition that comprises an aqueous solution of the multivalent metal source (i.e. the multimetal oxide of the multivalent metal, the hydroxide of the multivalent metal or the salt of the multivalent metal), such that the cross-linking composition comprises an aqueous solution of negatively charged multivalent metal complex ions having a pH of at least 9.0. Expressed another way, in some embodiments, the cross-linking agent may comprise a trivalent metal compound, which is used in solubilised form. The solubilised trivalent metal compound may be pre-formulated in to a cross-linking composition.

In notable embodiments, the cross-linking agent further comprises either (a) sulphur and a sulphur donor, (b) a multivalent metal oxide or ionic cross-linking agent, (c) sulphur, a sulphur donor and an ionic cross-linking agent, or (d) sulphur donor.

Thus, in some embodiments, the present application provides a synthetic elastomeric glove with:
(a) a thickness at the palm of less than 0.05 mm;
(b) a modulus at 500% above 6.5 MPa; and/or
(c) an elongation at break below 700%, and comprising the cured product of a synthetic latex composition comprising a synthetic polymer and a cross-linking agent that includes a cross-linking composition, the cross-linking composition comprising an aqueous solution of a multimetal oxide of a multivalent metal, a hydroxide of a multivalent metal or a salt of a multivalent metal, such that the cross-linking composition comprises an aqueous solution of negatively charged multivalent metal complex ions having a pH of at least 9.0.

Expressed in alternative terms, in some embodiments the present application provides a synthetic elastomeric glove with:
(a) a thickness at the palm of less than 0.05 mm;
(b) a modulus at 500% above 6.5 MPa; and/or
(c) an elongation at break below 700%, comprising a synthetic polymer and a cross-linking agent, wherein the cross-linking agent comprises a solubilised trivalent metal compound having a pH of at least 9.

The cross-linking agent in the above embodiment may further comprise sulphur, a sulphur donor (i.e. an accelerator) and a divalent metal oxide. The amount of each additional cross-linking agent may be less than 1.0 phr, preferably not more than 0.9, 0.8, 0.7, 0.6, 0.5 or 0.4 phr.

Where reference is made to a glove having features (a), (b) and/or (c), this means that feature (a) is present, and one or both of features (b) and (c) are present. In notable embodiments, the synthetic elastomeric glove comprises both of features (b) and (c), being the modulus and elongation at break properties.

In some embodiments, the synthetic elastomeric gloves have a palm zone surface roughness (as indicated by the $S_z$ value) of between −26-41 µm.

Also described herein is a glove-shaped former comprising (i) a palm zone, (ii) a cuff zone, (iii) between finger zones and (iv) finger zones, wherein:

the surface roughness ($S_z$) of the palm zone of the former is between 28 and 42 µm; and/or the cuff zone of the former includes a textured cuff band region.

In one embodiment, the glove-shaped former has a palm zone surface roughness ($S_z$) between 28 and 42 µm. This former may be referred to as a controlled roughness former. The palm zone surface roughness may be measured as a single surface roughness measurement taken at one location in the palm zone, but in preferred embodiments, the palm zone surface roughness is measured as an average of a plurality of roughness measurements taken at a plurality of locations in the palm zone. Preferably the surface roughness is the average of 4 roughness measurements taken at 4 different locations in the palm zone. The surface roughness in some embodiments is between 28 and 40 µm, such as 29-40 µm, 30-38 µm, 30-36 µm, 29-36 µm or 29-34 µm.

In some embodiments, the cuff zone also has a surface roughness ($S_z$) within the range of 28-42 µm. The preferred ranges are between 29-40 µm, 30-38 µm, 30-36 µm, 29-36 µm or 29-34 µm. Like the palm zone surface roughness measurements, the cuff zone surface roughness measurement may be taken at a single location in the palm zone, or the measurement may be based on an average of a plurality of measurements, suitably 4.

In another embodiment, there is described a glove-shaped former comprising a cuff zone including a cuff band region. The cuff band region may have a surface roughness (Si) that is greater than that of the cuff zone outside the cuff band region, or the cuff band region may comprise a visually observable textured area (i.e. a roughened, scored or otherwise textured surface) that resists or prevents slippage of a gelled latex on the former. This former may be referred to as a cuff-banded former. The cuff-banded former provides resistance to slipping of a gelled latex composition on the former during a pre-leaching stage of glove production. Such a feature is of particular pertinence to the production of ultra-thin film gloves, where it has been found that there is a greater tendency for slippage.

The present application also describes a method of manufacturing synthetic elastomeric gloves comprising:

dipping a former as described above into an elastomeric film-forming composition;

curing the elastomeric film-forming composition on the former so as to produce the synthetic elastomeric glove.

The present application also describes gloves produced on the formers described above, and by the methods described above.

BRIEF DESCRIPTION OF THE DRAWINGS

The present invention will now be described in further detail with reference to the following figures which illustrate non-limiting examples of aspects of the invention.

DETAILED DESCRIPTION

Figure 1:
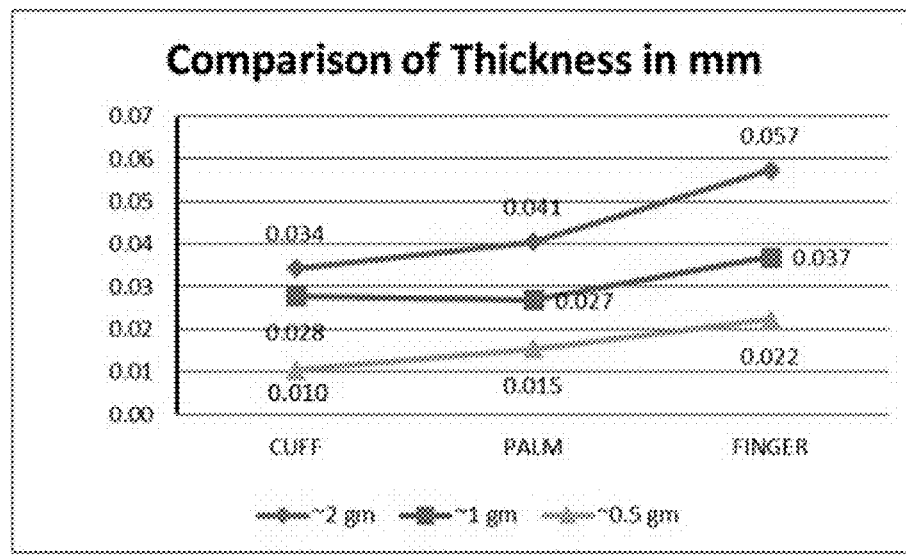
FIG. 1 is a graph comparing the thickness at the cuff, palm and finger of gloves of 2 g, 1 g or 0.5 g in accordance with embodiments of the present invention.
Figure 2:
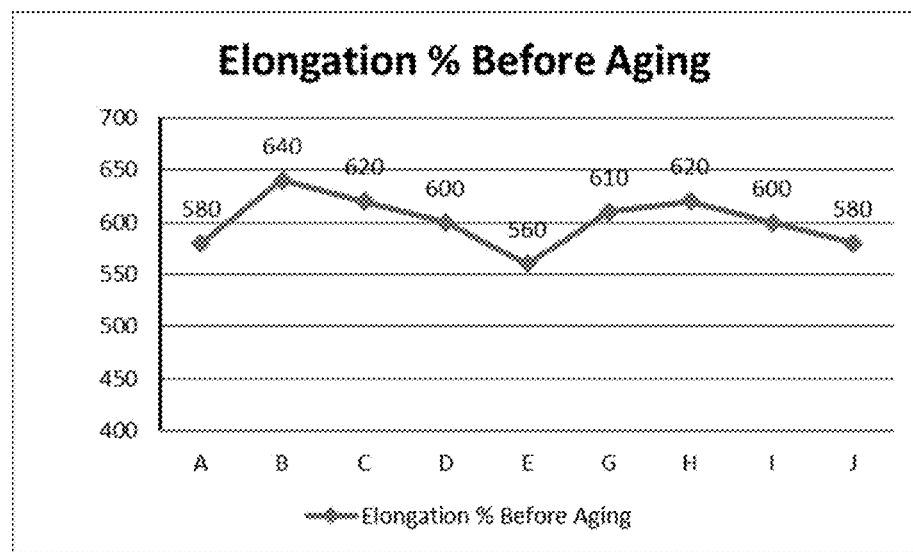
FIG. 2 is a graph showing the elongation of gloves of 2 g, made using unaged compositions A to J in accordance with embodiments of the present invention.
Figure 3:
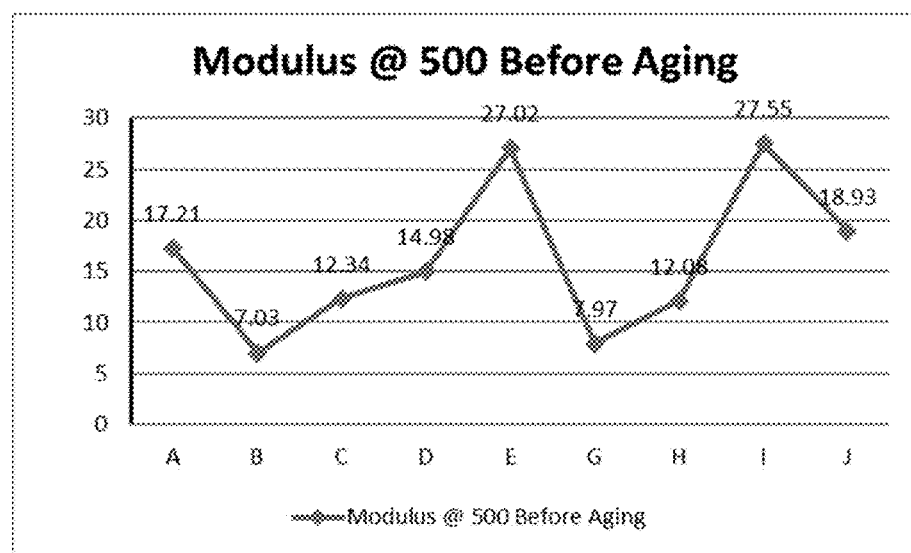
FIG. 3 is a graph showing the modulus at 500 of gloves of 2 g, made using unaged compositions A to J in accordance with embodiments of the present invention.

The synthetic elastomeric gloves and methods of manufacture are described in further detail in this section. Also described are new former types that may be used in the production of synthetic elastomeric gloves.

Glove Properties

The gloves of the present application may be classified or described as being disposable gloves, examination gloves, surgical gloves, medical gloves, laboratory gloves, clean room gloves, gloves for food contact, food processing and/or biotechnical applications, household gloves, and so forth. The gloves are suitable for use in cleanroom applications. The gloves may be described as dipped thin film gloves.

The gloves may be single layered or multilayered. This refers to the number of elastomeric film layers. In the case of multilayered gloves, there may be two elastomeric film layers to maintain the thin film properties and low weight, although it is possible for there to be additional elastomeric film layers provided each layer is very thin. Coating layers may also be applied, such as slip coatings or powder coatings to aid donning.

When calculating the overall thickness of elastomeric gloves, the standard practice in the industry (as established by the relevant standard D6319) is to measure the thickness of the glove at three points—the cuff, the palm and the finger. The finger thickness is measured 13 mm+/−3 mm from the fingertip; the palm thickness is measured at the centre of the palm, and the cuff thickness is measured at 25 mm+/−5 mm from the cuff edge. The average of the three measurements is taken to establish a glove thickness. Thickness measurements are taken in accordance with the procedure specified in ASTM D3767-03 (Reapproved 2014).

The thickness as measured at each of these three points can be close together (e.g. the thickness measured could be 0.05 mm at each point), or there can be greater variation between the thickness measurements at each point (e.g. the palm and cuff could be about 0.05 mm and the finger could be 0.08 mm). The finger thickness may be higher than the thickness measured at the cuff and palm, particularly if the glove mould is shaped to create a "textured" or "dimpled" grip surface in the finger region of the glove. For a glove with a thickness that is approximately 0.050 mm at the finger based on a smooth surface, the addition of a textured or dimpled surface results in an increase in the measured thickness based on the peak thickness of up to an additional 0.010 mm or 0.020 mm. At the cuff, the measured thickness can be either lower or higher than the measurements taken at the palm and the finger. The cuff may be of a lower thickness in some embodiments, particularly where the cuff is shaped such that the latex layer that is applied in the dipping process is thinner than at the palm region. In other embodiments, the cuff thickness can be significantly higher—this can be achieved by using a series of coagulant dipping and water dipping steps, designed to leave a lower coagulant concentration on the mould at all areas other than the cuff region (which contains a higher coagulant concentration), so as to ensure a thicker latex layer is applied in the cuff. The palm region is the most important of the three measurement points to control within the low thickness range specified in the present application. Accordingly, for particular embodiments of the present application, the focus is on the palm thickness, and in more specific embodiments, the thickness at the cuff and/or the fingertip is also taken into account.

The thickness of the elastomeric glove at the palm (or the "palm thickness") is less than 0.05 mm. In some embodiments, the palm thickness may be in the range of 0.005 mm to less than 0.050 mm. The palm thickness may, for example, be a minimum of 0.005 mm, 0.007 mm, 0.010 mm, 0.015 mm, 0.020 mm, 0.025 mm, 0.030 mm, 0.035 mm, 0.040 mm or 0.045 mm. The thickness may be a maximum of 0.048 mm, 0.045 mm, 0.040 mm, 0.035 mm, 0.030 mm, 0.028 mm or 0.025 mm. Any minimum and maximum can be combined to form a range, provided the minimum value is below the maximum value. In some embodiments, the palm thickness is between 0.010 mm and less than 0.050 mm, or between 0.015 mm and 0.045 mm, or between 0.020 mm and 0.041 mm. In alternative embodiments, the palm thickness can be 0.050 mm or higher (up to 0.080 mm), particularly if the glove has a lower cuff and finger thickness, such that the average of the three is below 0.050 mm.

In some embodiments, the thickness of the elastomeric glove at the cuff (or the "cuff thickness") is less than 0.05 mm. The cuff thickness may be in the range of 0.005 mm to less than 0.050 mm. The cuff thickness may, for example, be a minimum of 0.005 mm, 0.007 mm, 0.008 mm, 0.010 mm, 0.015 mm, 0.020 mm, 0.025 mm, 0.030 mm, 0.035 mm, 0.040 mm or 0.045 mm. The cuff thickness may be a maximum of 0.048 mm, 0.045 mm, 0.040 mm, 0.035 mm, 0.030 mm, 0.028 mm or 0.025 mm. Any minimum and maximum can be combined to form a range, provided the minimum value is below the maximum value. In some embodiments, the cuff thickness is between 0.008 mm and less than 0.050 mm, or between 0.008 mm and 0.040 mm, or between 0.010 mm and 0.040 mm. In alternative embodiments, the cuff thickness could be up to 0.080 mm thick. In such alternative embodiments, the palm and finger thickness is typically lower, such that the average thickness across the three points is below 0.050 mm.

In some embodiments, the thickness of the elastomeric glove at the finger (or the "finger thickness") is 0.080 mm or less, such as 0.070 mm or less. As noted above, the finger thickness measurement may be higher than for other parts of the glove, particularly if the glove has a "textured" or "dimpled" grip surface in the finger region of the glove. The textured region may contain peaks and troughs, with the peaks being up to an additional 0.010 mm or 0.020 mm thicker than the troughs. The finger thickness may be in the range of 0.005 mm to 0.070 mm. The finger thickness may, for example, be a minimum of 0.005 mm, 0.008 mm, 0.010 mm, 0.015 mm, 0.020 mm, 0.025 mm, 0.030 mm, 0.035 mm or 0.040 mm. The finger thickness may be a maximum of 0.070 mm, 0.060 mm, 0.055 mm, 0.050 mm, less than 0.050 mm, 0.048 mm, 0.045 mm, 0.040 mm, 0.035 mm, 0.030 mm, 0.028 mm or 0.025 mm. Any minimum and maximum can be combined to form a range, provided the minimum value is below the maximum value. In some embodiments, the finger thickness is between 0.010 mm and less than 0.060 mm, or between 0.015 mm and 0.060 mm, or between 0.015 mm and 0.050 mm. Where the finger thickness is 0.050 mm and above, preferably the average thickness across the three points (finger, palm and cuff) is below 0.050 mm.

In some embodiments, the average of the palm and finger thicknesses is below 0.050 mm. The average of the palm and finger thicknesses may be in the range of 0.005 mm to less than 0.050 mm. The average thickness may, for example, be a minimum of 0.005 mm, 0.007 mm, 0.010 mm, 0.015 mm, 0.020 mm, 0.025 mm, 0.030 mm, 0.035 mm, 0.040 mm or 0.045 mm. The average thickness may be a maximum of 0.048 mm, 0.045 mm, 0.040 mm, 0.035 mm, 0.030 mm, 0.028 mm or 0.025 mm. Any minimum and maximum can be combined to form a range for the average of the palm and finger thicknesses, provided the minimum value is below the maximum value. In some embodiments, the average thickness is between 0.010 mm and less than 0.050 mm, or between 0.015 mm and 0.045 mm, or between 0.020 mm and 0.040 mm.

In some embodiments, the average of the palm and cuff thicknesses is below 0.050 mm. The average of the palm and cuff thicknesses may be in the range of 0.005 mm to less than 0.050 mm. The average thickness may, for example, be a minimum of 0.005 mm, 0.007 mm, 0.010 mm, 0.015 mm, 0.020 mm, 0.025 mm, 0.030 mm, 0.035 mm, 0.040 mm or 0.045 mm. The average thickness may be a maximum of 0.048 mm, 0.045 mm, 0.040 mm, 0.035 mm, 0.030 mm, 0.028 mm or 0.025 mm. Any minimum and maximum can be combined to form a range for the average of the palm and cuff thicknesses, provided the minimum value is below the maximum value. In some embodiments, the average thickness is between 0.010 mm and less than 0.050 mm, or between 0.015 mm and 0.045 mm, or between 0.020 mm and 0.040 mm.

According to another aspect of the present application, there is provided a synthetic elastomeric glove with:
  (a) a thickness based on the average of the palm, cuff and finger thicknesses of less than 0.05 mm;
  (b) a modulus at 500% above 6.5 MPa; and/or
  (c) an elongation at break below 700%.

Preferably both the modulus and elongation at break are within the ranges indicated (i.e. the glove has features (b) and (c)). In some embodiments, the average thickness (based on the average of the palm, cuff and finger thicknesses) is in the range of 0.005 mm to less than 0.050 mm. The average thickness may, for example, be a minimum of 0.005 mm, 0.007 mm, 0.010 mm, 0.015 mm, 0.020 mm, 0.025 mm, 0.030 mm, 0.035 mm, 0.040 mm or 0.045 mm. The average thickness may be a maximum of 0.048 mm, 0.045 mm, 0.040 mm, 0.035 mm, 0.030 mm, 0.028 mm or 0.025 mm. Any minimum and maximum can be combined to form a range for the average thickness, provided the minimum value is below the maximum value. In some embodiments, the average thickness is between 0.010 mm and less than 0.050 mm, or between 0.010 mm and 0.045 mm, or between 0.015 mm and 0.040 mm.

The thickness of the elastomeric film glove is measured, at any point of measurement specified in the present application, in accordance with the standard procedure known in the art. The measurement procedure is set out in ASTM D3767-03 (Re-revised 2014). In simple terms, the procedure involves measuring the thickness based on the median of three measurements made on each test specimen with a micrometer. The micrometer may be analogue or digital. The present applicant used each of a Mitutoyo analog micrometer, model 7301, or a Mitutoyo digital micrometer, model PK-101. The exact location for taking the thickness measurements for the palm, cuff and finger is set out in ASTM D 6319-10

Elastomeric gloves come in a number of lengths, which is largely dependent on the cuff or sleeve length. The length of a glove is measured from the longest fingertip to the end of the cuff. One standard glove length is 9 inches (229 mm), and another is 12 inches (305 mm). The length of gloves of embodiments of the present application may therefore be between 200 mm-330 mm.

Based on such length dimensions, the weight of the glove having the thickness as indicated above should be not more than 2.8 grams for a 12 inch (305 mm) glove (e.g. for a glove between 270 and 330 mm in length), and 2.2 grams or less for a 9 inch (229 mm) glove (e.g. for a glove between 200 and 270 mm in length).

In one particular embodiment of the present application, there is provided a synthetic elastomeric glove with:
  (a) a weight of not more than 2.4 grams for a glove length of 200 to 270 mm, or a weight of not more than 2.8 grams for a glove length of 270 to 330 mm;
  (b) a modulus at 500% above 6.5 MPa; and/or
  (c) an elongation at break below 700%.

Preferably both of features (b) and (c) are present. In some embodiments, the gloves have a weight of not more than 2.4 grams. The weight may be a minimum of 0.3 grams. In some embodiments, the glove weight may be a maximum of 2.3 grams, 2.2 grams or 2.1 grams. In some embodiments the glove weight is a minimum of 0.3 g, 0.4 g 0.5 g, 0.7 g, or 1.0 g. The glove weight in some embodiments is about 0.5 grams, 1.0 grams, 1.5 grams or 2.0 grams. The value may be +/−0.2 g, thus covering 0.5 grams+/−0.2 grams, 1.0 grams+/−0.2 grams, or 2.0 grams+/−0.2 grams. In alternative embodiments, suited to the longer length gloves, the weight is 2.8 grams or less, such as a maximum of 2.7 grams, 2.6 grams, 2.5 grams or 2.4 grams. The minimum weight may be any of those indicated above in this paragraph.

The weight information is based on a medium glove size. Medium sized gloves have a palm width of 90 to 99 mm, preferably 94-98 mm. Disposable gloves are conventionally sold in a selection of sizes—extra-extra-small (XXS), extra-small (XS), small (S), medium (M), large (L), extra-large (XL) and extra-extra-large (XXL). The palm widths vary for each size. It will be appreciated that there are conventional dimensions for gloves within each size range, and the setting of a weight range that is applicable to the medium size allows for valid comparisons to be made. Nevertheless, in some embodiments, the glove weight requirements apply irrespective of the size of the glove.

The elastomeric glove of an embodiment of the present application has a modulus at 500% above 6.5 MPa. The modulus at 500% may be greater than 7.0, 8.0, 9.0, 10, 12, 15, 20 or 25. The modulus may in some embodiments be a maximum of 20. When combined with a minimum value, the minimum is below 20. The modulus values may be based on the unaged variant, but is preferably based on the aged variant, or both the unaged and aged variants. Having this modulus value for an ultra-thin glove (i.e. less than 0.05 mm in thickness at palm) has been achieved for the first time.

The elastomeric glove of the present application has an elongation at break below 700%. The gloves of the present application have this elongation value combined with the previously described ultra-low weight (and thickness), and with the above modulus value at 500%. The elongation at break may be at less than 680%, 660%, 650%, 640%, 630%, 620%, 610% or less than 600%. The elongation at break is typically greater than 200%, such as greater than 250%, or greater than 300%.

The elastomeric glove of the present application preferably also meets or exceeds ASTM D6319-00a for water leakage. Despite having a thickness below that set by ASTM D6319-00a, the present gloves meet this water leakage test.

The calculations of weight, thickness, modulus and elongation may be based on a sample of at least 10 gloves.

The synthetic elastomeric gloves suitably have a palm zone surface roughness (Si) of between 26-41 µm. This surface roughness is indicative of the glove having been produced on a former with a controlled palm surface roughness that is slightly higher than the glove surface roughness—for instance, a former with a palm zone surface roughness between 28 and 42 µm.

The palm zone surface roughness $S_z$ of the glove may be a minimum of 26, 27, 28, 29, 30, 31 or 32 µm. The palm zone surface roughness $S_z$ of the glove in some embodiments is not more than 41, 40, 39, 38, 37, 36, 35, 34, 33 or 32 µm. Each minimum and maximum can be combined to form a suitable range for the palm zone surface roughness of the glove, such as 27-38 µm, 28-36 µm, 28-34 µm, 27-34 µm or 27-32 µm.

The palm zone surface roughness comes about as a consequence of the production of the glove on a former with a corresponding surface roughness in the same zone. As explained in further detail below, such controlled roughness formers having a controlled palm zone surface roughness contribute to the production of high quality ultra-low thickness gloves. The surface roughness ($S_z$) of the glove in the palm zone of the glove is typically around 1-10 µm, 1-7 µm, 2-6 µm or 1-3 µm less than the surface roughness of the former in the same zone.

Throughout this specification, the surface roughness has been measured using a Keyence VHX-6000 High Resolution Digital Microscope. This is operated to determine the $S_z$ value in accordance with ISO 25178 (non-contact probe). A suitable lens for determining the surface roughness in the required scale is the Z100 lens, at between 400× and 500× magnification.

As outlined in further detail below, the applicant has been able to produce on a commercial scale for the first time low thickness gloves with very low defect rates. In fact, in a test production run of 21 days duration, with 4 formers producing 96 pieces per day (24 cycles of approximately 55 minutes duration per day), there was a zero level pin-hole defect rate. All 2016 gloves were tested and found to be free of pin-hole defects. This result is remarkable for such a low thickness product.

Elastomers

The elastomeric film-forming composition comprises an elastomeric film-forming polymer (or polymer for short), in suspension or emulsion form. The polymer is a synthetic polymer, in that natural rubber (natural isoprene) is not within the range of polymers to which this application applies. The polymer used in the preparation of the elastomeric gloves may be selected from synthetic elastomeric film-forming polymers which can be cross-linked to produce elastomeric gloves. The polymer may be a single polymer or a combination (blend) of two or more polymers. The or each polymer may be a homopolymer or a copolymer, a grafted or modified polymer, or a blend thereof. Blends may contain between 1-99% of each component of the blend, with the total amount of polymers adding up to 100% (based on polymer content). The number of polymers in a blend is typically two or three.

The polymer may contain free ionically cross-linkable groups, covalently cross-linkable groups, or a combination of both. Examples of ionically cross-linkable groups are acids, including carboxylates (and esters), sulfonates and acid anhydrides, and an example of a covalently cross-linkable group is a double bond. In some embodiments, the polymer of the elastomeric film-forming composition, or at least one of the polymers in the case of a blend, comprises both ionically cross-linkable groups and covalently cross-linkable groups.

The polymers may be selected from nitrile rubber, polyurethane, polyisoprene, polychloroprene, acrylic polymers (including acrylic diene block copolymers), polybutadienes, copolymers of these and other polymers/monomers (random copolymers, block copolymers or otherwise) and modified forms of these polymers or copolymers (e.g. polymers containing additional substituents such as carboxylate, sulfonate, halide or other substituents).

One class of polymer that may be used is that obtained by copolymerisation of conjugated diene monomers and ethylenically unsaturated acid monomers (carboxylated polyacrylonitrile butadiene being an example of such a copolymer), polyisoprene, polychloroprene, styrene copolymers and/or polyurethane. Amongst the range of conjugated diene monomers, examples are 1,3-butadiene, isoprene, 2,3-dimethyl-1,3-butadiene, 2-ethyl-1,3-butadiene, 1,3-pentadiene, chloroprene and acrylonitrile. Regarding ethylenically unsaturated acid monomers, the acid group may be a carboxyl group, a sulfonic acid group or an acid anhydride group. Examples of ethylenically unsaturated acid monomers include acrylic acid or methacrylic acid; itaconic acid, maleic acid, fumaric acid, maleic anhydride, citraconic anhydride, styrenesulfonic acid, monobutyl fumarate, monobutyl maleate, mono-2-hydroxypropyl maleate, and alkali metal or ammonium salts thereof. The polymers used may be carboxylated or non-carboxylated, as desired.

In some embodiments, the polymer used in the present application is a carboxylated polymer. The synthetic carboxylated polymer may be selected from the group consisting of carboxylated nitrile butadiene rubber, carboxylated styrene butadiene rubber, carboxylated butyl rubber, carboxylated acrylic butadiene rubber, carboxylated polyisoprene, carboxylated polychloroprene, and mixtures or copolymers thereof.

In some embodiments, the synthetic carboxylated polymer is carboxylated acrylonitrile butadiene polymer, or a co-polymer of this polymer, or a mixture of this polymer with a second polymer.

One notable example of a suitable polymer is polyacrylonitrile butadiene. This may be carboxylated or non-carboxylated. In one embodiment the polymer is a carboxylated acrylonitrile butadiene rubber. In one particular form, the carboxylated acrylonitrile butadiene rubber has a medium acrylonitrile content. Examples of suitable polymers include those supplied by Synthomer, Nippon-Zeon, Nantex, Shin-Foong, Khumho, BST and others, noting that the grades to be selected from are those indicated as being suitable for dipped articles, such as gloves and similar products.

Carboxylated refers to the presence of carboxylate (carboxylic acid or ester) groups on the polymer chain. Carboxylation may be achieved by forming the polymer with a monomer containing carboxylate groups, or through grafting carboxylate groups to a polymer.

The degree of carboxylation of the polymer may influence the decision as to what cross-linking agents are required. The carboxylation degree may be at the higher end (between 5-15%; more typically 5-10%), or at the lower end (between 0.01-5%).

When producing the gloves using a dipping process, the polymer is provided initially in the form of an aqueous suspension. The aqueous suspension suitably has a pH of at least 9.0. The elastomeric film-forming composition can also be referred to as the "synthetic latex composition" or "latex composition". It is common in the art to use the expression "latex" or "rubber" to refer to any polymer in a general sense, and "latex composition" is used in a corresponding manner. Latex is not to be read as referring to natural rubber latex.

In the art of the present invention, it is common to refer to the amount of the elastomer-forming polymer as being 100 phr (per hundred parts "rubber"), and for the relative amounts of the remaining components of a composition for producing an elastomeric film to be calculated as a number of parts compared to the 100 phr of the elastomer-forming polymer, by weight. Thus, for an amount of cross-linking agent that is 1/100 that of the elastomer-forming polymer in the composition by weight, the amount of cross-linking agent is referred to as 1.0 phr.

Cross-Linking Agents

Cross-linking agent classes include ionic cross-linking agents and covalent cross-linking agents. The cross-linking agent or agents used in the production of the elastomeric gloves may be selected from ionic cross-linking agents, covalent cross-linking agents, and combinations thereof.

Ionic cross-linking agents include metal oxide cross linking agents (such as zinc oxide and magnesium oxide), peroxides (such as 1,1-di(t-butylperoxy)-3,3,5-trimethylcyclohexane, which can be purchased under the trade name Trigonox 29-40B-pd) and solubilized ionic cross-linking agents such as the trivalent metal compounds, including multimetal oxides of multivalent metals (e.g. solubilized sodium aluminate), multivalent metal hydroxides, and multivalent metal salts. Other ionic cross-linking agents amongst those known in the art and be used.

Covalent cross-linking agents include organic cross-linking agents, sulphur and/or sulphur donors, and combinations thereof.

Sulphur may be added in the form of elemental sulphur. Sulphur may be added in the form of a sulphur donor. Examples of suitable sulphur donors include the carbamates such as thiocarbamates (e.g. zinc dibutyl dithiocarbamate (ZDBC), Zinc diethyl dithiocarbamate (ZDEC); Zinc dimethyl dithiocarbamate (ZDMC); thiurams (eg. tetraethylthiuram disulfide (TETD), Tetramethyithiuram disulphide (TMTD)); Dipentamethylene thiuram tetrasulfide (DPTT); Dipentamethylene thiuram hexasulfide (DPTH); Dipentamethylene thiuram hexasulfide; thiourea (Ethyl thiourea (ETU) and diphenylthiourea (DPTU); thiazoles (e.g. Mercapto Benzothiazoles (MBT), Mercapto Benzothiazole disulphide (MBTS), zinc 2-mercaptobenzothiazole (ZMBT)); guanidines (eg. Diphenylguanidine (DPG)) and aldehyde/amine-based Sulphur donors (eg. hexamethylenetetramine). Other examples are well known in the art and can be obtained from various publicly available sources.

Other cross-linking agents that may be used can be selected from crosslinking monomers, reactive oligomers, polyisocyanate oligomers, functional crosslinkable polymers, derivatives of ethylene glycol di(meth)acrylate (such as ethylene glycol diacrylate, di(ethylene glycol) diacrylate, tetra(methylene/ethylene glycol) diacrylate, ethylene glycol dimethacrylate (EDMA), di(ethylene glycol) dimethacrylate (DEDMA), tri(methylene/ethylene glycol) dimethacrylate, tetraethylene glycol dimethacrylate (TEDMA)), derivatives of methylenebisacrylamide (such as N,N.-methylenebisacrylamide, N,N.-methylenebisacrylamide, N,N.-(1,2 dihydroxyethylene)bisacrylamide), formaldehyde-free cross-linking agents (such as N-(1-Hydroxy-2,2-dimethoxyethyl) acrylamide), divinylbenzene, divinylether, diallyl phthalate, divinylsulfone, Trimethylolpropane Trimethacrylate (TMPTMA), polyfunctional cross-linkers and the like. Combinations of these cross-linking agents can also be used.

The total amount of cross-linking agents in the composition may be between 0.01 and 14 phr. However, it is usually desirable to minimise cross-linker amounts (and the associated costs or disadvantages). The total cross-linking agent amount may be within one of the following ranges: 0.01-14.5 phr, 0.2-12.5 phr, 0.3-10 phr, 0.1-10 phr, 0.2-10 phr, 0.3-9 phr, 0.5-9 phr, 0.8-9 phr, 0.3-8 phr, 0.5-8 phr, 0.8-6 phr, 1-5 phr, 2-9 phr, 3-10 phr, 3-7 phr, 1-3 phr, 0.01-0.5 phr, 0.01-1.0 phr. In one embodiment, the synthetic elastomeric glove is made from a synthetic latex composition containing a small amount of cross-linking agent or a combination of cross-linking agents, where the total amount of cross-linking agent(s) present in the composition is less than 5.0 phr, less than 4.0 phr, less than 3.0 phr, less than 2.5 phr, less than 2.0 phr, less than 1.8 phr or less than 1.5 phr.

The amount of ionic cross-linking agent may be between 0.0-5.0 phr, such as 0.01-5.0, or 0.01-4.0 phr. The amount is preferably lower still, at 0.01-3.0 phr, or 0.01-2.0 phr, 0.01-1.0 phr, 0.01-0.7 phr, 0.01-0.6 phr or 0.01-0.5 phr. Within the amount of ionic cross-linking agent, there may be a solubilised trivalent metal cross-linking agent in an amount of 0.01-0.6, 0.01-0.5 or 0.01-0.45 phr, and a divalent metal oxide within an amount of 0.01-0.8, preferably 0.01-0.6, 0.01-0.5 phr.

The amount of sulphur may be between 0.0-5.5 phr. The amount may be lower still, at 0.0-3.5 phr, such as 0.01-3.0 phr, 0.01-2.0 phr, 0.01-1.5 phr, 0.01-1.0 phr, 0.01-0.7 phr, 0.01-0.5 phr or 0.01-0.3 phr.

The amount of sulphur donor (accelerator) may be between 0.0-2.0 phr, such as between 0.01-1.5 phr, 0.01-1.0 phr, 0.2-1.0 phr, 0.01-0.7 phr, 0.01-0.5 phr, 0.01-0.3 phr or 0.05-0.2 phr, The amount of organic cross-linking agent may be between 0.0-4.0 phr, such as 0.01-4.0. The amount may be lower still, at 0.01-3.0 phr, or 0.01-2.0 phr, or 0.01-1.0 phr. In some embodiments, the cross-linking agent is free of organic cross-linking agents other than sulphur and sulphur donors.

The cross-linking agent can be combined with the latex composition and other components of the elastomeric film-forming composition at suitable time points for the formation of the desired type of film. Cross-linking agents are typically added to the latex composition with other components, however for some forms of cross-linking agent (such as the solubilised ionic cross-linking agents, including sodium aluminate) there is a preliminary step involving the formation of a cross-linking composition and combining this with the latex under controlled conditions, followed by the addition of other components and secondary cross-linking agents.

Cross-Linking Composition

In some embodiments, the cross-linking agent comprises a cross-linking composition, which comprises an aqueous solution of a negatively-charged multivalent metal complex ion having a pH of at least 9.0. Expressed another way, the cross-linking composition is based on an aqueous solution of a metal co-ordination complex, in which the metal is a multivalent metal, there are ligands co-ordinating to the central metal ion, and the overall complex is negatively charged. An example of such a negatively charged multivalent metal complex ion is $[Al(OH)_4]^-$, which is based on an aluminium metal ion, four hydroxide ligands co-ordinated to the metal, and an overall negative charge. There may be a cation counterion such as $Na^+$ in the solution. Such solutions can be formed through the dissolution of a multimetal oxide of a multivalent metal, a multivalent metal hydroxide, or a multivalent metal salt in water. In the case of $[Al(OH)_4]^-$, this may be produced on solubilisation of sodium aluminate under appropriate conditions. Those conditions may include stabilisation with a hydroxide (i.e. an alkali in hydroxide form). This so-called "cross-linking composition" may be formed from the multimetal oxide of a multivalent metal, a multivalent metal hydroxide, or a multivalent metal salt prior to combining with other components of the elastomeric film-forming composition. A hydroxide (an alkali in hydroxide form) may be required to maintain the negatively-charged multivalent metal complex ion in solution form without significant precipitation. Additional cross-linking agents may be used with this cross-linking agent/cross-linking composition. The ligands in the complex may be of any suitable type. Notable examples are hydroxide and water. It is possible that other ligands could be present in suitable metal complexes, such as one or more of hydroxide, water, iodide, bromide, sulphide, thiocyanate, chloride, nitrate, fluoride, oxalate, oxo, nitrile isothyacyanate, acetonitrile, ammonia and nitrate.

In simple terms, in one embodiment, the cross-linking composition may comprise a solubilised trivalent metal compound, such as a solubilised aluminium compound. Examples include sodium aluminate, aluminium oxide and aluminium hydroxide. The composition may comprise additional hydroxide compound, for pH adjustment to achieve solubilisation, such as sodium hydroxide, potassium hydroxide and/or ammonium hydroxide. The amount of such additional hydroxide may be at least 0.05 phr, 0.1 phr, or 0.2 phr, or 0.3 phr, by way of example. The cross-linking composition may further comprise a mechanical stabiliser and/or surfactant, as is further described herein.

Sodium aluminate is a notable example of a multimetal oxide of a multivalent metal, where the multivalent metal is aluminium. Through the techniques described herein, this can be solubilised so as to produce a solution of negatively-charged multivalent metal complex ions. Whilst embodiments of the invention are based on sodium aluminate, it is noted that other agents within the same class can be used. In this portion of the detailed description, reference is made to the example of negatively-charged aluminium complex ions, and sodium aluminate as a source for those ions. However, this should be read in this context and should not be understood as confining the scope of the invention.

The present inventors have managed to produce ultra-thin elastomeric film gloves with good performance properties using the solubilised form of multivalent metal cross-linking agent. When using solubilised multivalent metal cross-linking agent (such as solubilised sodium aluminate), it is important to solubilise the multivalent metal with an alkali (i.e. an alkali hydroxide) in a preliminary step, rather than adding the multivalent metal (e.g. sodium aluminate) in solid form to the aqueous suspension of synthetic polymer, followed by separate addition of alkali hydroxide to attempt to solubilise the multivalent metal in a later step. The amount of alkali hydroxide used to solubilise the multivalent metal is preferably about 0.05-0.5 phr. Once solubilised (forming a so-called cross-linking composition), the composition is added in a controlled manner to the aqueous suspension of synthetic polymer. The aqueous suspension may also be subjected to pH control. The streams are carefully combined while avoiding disruption of the emulsion, latex lump formation through micro-coagulation, precipitation or other settling of the components from the composition.

Multivalent Metal

The term "multivalent metal" refers to a metal having a valency of two or more. The expression "divalent or higher valency" may be used interchangeably with "multivalent". In some embodiments, the multivalent metal is a trivalent metal.

Aluminium is the preferred multivalent metal. In other embodiments the multivalent metal is an amphoteric metal. Amphoteric metals are those metals that form amphoteric substances from their oxides and/or hydroxides. This class includes aluminium, beryllium, chromium, zinc, copper, iron, cobalt, lead, tin, bismuth, gallium, indium, scandium, titanium, zirconium, vanadium, silver, gold, germanium, antimony and tellurium. The multivalent metal is preferably selected from the group consisting of aluminium, beryllium, chromium, iron, cobalt, copper, zinc, lead, tin and bismuth. The multivalent metal may be selected from aluminium and beryllium. Trivalent (or higher valency) metals are preferred, and aluminium is most preferred in selected embodiments.

To produce a cross-linking composition, initially a solution is formed by dissolving a source of the multivalent metal in water. This may be achieved with heating and the optional addition of an alkali and/or a mechanical stabiliser and/or a surfactant. A mechanical stabiliser and/or surfactant may be included in the cross-linking composition.

A suitable source of the multivalent metal should be chosen that is capable of yielding a solution of negatively charged multivalent metal complex ions. This may require pH adjustment of the solution to achieve solubilisation. Suitable sources included (A) a multimetal oxide of the multivalent metal, (B) a hydroxide of the multivalent metal or (C) a salt of the multivalent metal.

Regarding the first class, being the multimetal oxides of the multivalent metal, this term refers to an oxide of the multivalent metal with another one or more different metal species. These may be referred to as "multimetal oxides" in short. Such materials may also be viewed as mixed metal oxides. Where there are two metals, the oxide may be described as a double metal oxide. The second metal species may be, for example, an alkali metal, such as sodium or potassium. In the case of aluminium as the multivalent metal, the second metal species is preferably sodium or potassium, also referred to as sodium aluminate and potassium aluminate. In one example, the multimetal oxide of the multivalent metal may be an alkali metal-multivalent metal oxide.

The second class, being hydroxides of the multivalent metal, may simply be referred to as metal hydroxides. In practice, to achieve the production of the negatively charged multivalent metal complex ion, a second hydroxide (such as an alkali metal hydroxide or other alkali in hydroxide form) is required, with a consequent increase in the pH required for solubilisation of the multivalent metal hydroxide. The hydroxides of the multivalent metals may in some cases be viewed as the hydrated multivalent metal oxides, and the source of the multivalent metal hydroxide may in practice be a multivalent metal oxide (particularly a mixed metal oxide). In solution, there may be a mixture of different hydroxides of the multivalent metal, in different complex ion forms.

The third class, being the salts of the multivalent metals, typically require considerable alkali/hydroxide addition (such as alkali metal hydroxide or other alkali in hydroxide form) to achieve solubilisation of the multivalent metal and production of the negatively charged multivalent metal complex ions. Solutions of multivalent metal salts are not typically alkaline, and it may be necessary to add considerable alkali (alkali in hydroxide form) to raise the pH to at least 9.0. It is important in such cases for the negatively charged multivalent metal complex ions to be produced on raising the pH, without significant precipitation of an insoluble salt. Examples of salts include alum (potassium alum, or potassium aluminium sulphate), poly aluminium chloride (also referred to as $AlCl_3$), and poly ferric sulphate. The pH of 10% solutions of these salts are 2.83, 3.27 and 1.7, respectively, so considerable alkali (in the form of alkali hydroxide) is required to raise the pH to at least 9.0 and to form the negatively charged multivalent metal complex ions.

The first two classes are preferred, thus it is preferred that the cross-linking composition comprises a solution of a multimetal oxide of the multivalent metal or a solution of a multivalent metal hydroxide.

As indicated above, in some embodiments, the cross-linking composition comprises a solution of sodium aluminate, producing negatively-charged aluminium complex ions. The primary ions formed are the tetrahydroxoaluminate (III) ions—being a complex of a central aluminium atom with co-ordinating hydroxo ligands. Aqua (water) ligands may also form part of the complex ions. Other ions in the solution will include the aluminium and alkali metal (e.g. Na). The range of negatively charged aluminium complex ions produced on solubilising sodium aluminate is reported in the literature. At varying pH levels, the equilibrium between the various ions will differ. The key to maintaining soluble aluminium complex ions is to maintain the pH above 9.0, as below 9.0 insoluble $Al(OH)_3$ is formed, which precipitates out of solution. With other multivalent metals, the pH must be such that the soluble negatively-charged complex ions of the multivalent metal are formed, and an insoluble precipitate is minimised or avoided. In this regard, preferably not more than 20%, more preferably not more than 15%, 10%, 5% or less than 2% of the multivalent metal is in the form of an insoluble precipitate (precipitated out of solution). These percentages apply regardless of the source used, and regardless of the identity of the multivalent metal that is solubilised to form the negatively-charged multivalent metal complex ion.

Advantages associated with the use of sodium aluminate, or other solubilised cross-linking agent sources as described herein, are as follows:

There is no cost associated with milling (in contrast to solid zinc oxide and other prior art solid cross-linking agents). Thus, incorporating at least some sodium aluminate in solubilised form in the composition is associated with cost savings compared to compositions containing only solid cross-linking agents.

Aluminium has a low atomic weight of 27 and a specific gravity of 2.7. Per molecule that requires cross-linking, less weight of aluminium-based reagent is required compared to many other cross-linking agents.

Aluminium has a valency of 3, allowing for 3-links per molecule. In contrast, zinc, with a valency of 2, allows for 2-links per molecule. This allows for a theoretical 50% in the cross-linking ability of aluminium compared to zinc, even leaving aside the solubilising effect (compared to solid zinc oxide).

Aluminium in this form is not subject to purity concerns, allowing it to be used in a range of applications.

Aluminium is abundant, and safe for food applications (as reflected by the use of aluminium foil food packaging.)

In view of the effectiveness of the cross-linking with the solubilised multivalent metal, it is possible to produce products with lower amounts of sulphur and sulphur donor materials. This also applies to embodiments using multivalent metals other than just aluminium. It is possible to produce excellent low-weight gloves suitable for commercial production containing low levels of the solubilised multivalent metal oxide, hydroxide or salt, with low levels of the sulphur and sulphur donor (alone or with an ionic cross-linking agent), or sulphur donor alone.

Homogeneity is improved, as a consequence of lightness and the ionic nature of the negatively-charged complex. Intra-particle cross-links can be formed at a similar distribution to the inter-particle cross-links. Homogeneity can be further maximised through the use of stabilising agents, as described below.

Loss due to milling wastage is avoided. Loss due to settling during storage or in the dipping tank is avoided.

The multivalent metal, in aqueous ionic form, can instantly react with carboxylic groups on the polymer, where a carboxylated polymer is used as the elastomeric film-forming polymer. This can be achieved at room temperature, thus leading to potential cost savings associated with avoided heating. Whilst the cross-linking can be conducted at lower temperature (e.g. <40° C. or <30° C.), higher temperatures may still be used to achieve cross-linking of second cross-linking agent(s), if present.

Embodiments using low levels of aluminium-based solubilised cross-linking agents provide particularly good results with low input of total cross-linking agents (in phr).

Articles, such as gloves, made using the cross-linking composition and through the associated method have been found to possess highly favourable characteristics such as favourable feel and comfort, and improved softness. The gloves are made from a very thin layer (or layers) of elastomeric film without increasing the presence of defects such as pin holes, weak spots or other defects.

Gloves made from the product are easy to don.

It should be noted that zinc oxide is not an example of a suitable agent for producing a solubilised negatively-charged multivalent metal complex ions, even when the pH of the aqueous composition to which it is added has a pH of around 9.0-10.0. Zinc oxide is a metal oxide, rather than a mixed metal oxide, and even considerable alkali hydroxide addition to an aqueous composition containing zinc oxide is ineffective to produce solubilised negatively-charged multivalent metal complex ions. Whilst zinc oxide is not an example of an agent for forming the solubilised cross-linking composition, it may be used as an additional (secondary) cross-linking agent.

Alkali in Cross-Linking Composition and pH

In embodiments of the invention, the cross-linking composition further comprises alkali. The term "alkali" is used to refer to an agent or combination of agents that increase the pH of a solution. pH control may be the predominant function of the alkali. Typically, strong alkalis (e.g. hydroxides) are used for this purpose. The amount of alkali that forms part of the cross-linking composition is preferably between 0.01 and 5 phr. The maximum is preferably not more than 4, 3, 2 or 1 phr in the cross-linking composition (noting that there may be additional alkali in the latex composition). The amount may be a maximum of 0.9, 0.8, 0.7, 0.6, 0.5, 0.4 or 0.3 phr. The amount may be a minimum of 0.01, 0.05, 0.06, 0.07, 0.08, 0.09 or 0.1 phr. Any maximum and minimum may be combined to form a range. In some examples, the amount of alkali is between 0.01 and 0.5 phr, or between 0.01 and 0.4 phr, or between 0.05 and 0.5 phr. The alkali may be in the form of a hydroxide. This may be added in the form of sodium hydroxide, potassium hydroxide, ammonium hydroxide or a combination of two or more thereof. Sodium and/or potassium hydroxide are most typically used. The alkali serves to increase the pH to the level required for solubilisation and/or to chemically stabilise the solution of negatively charged multivalent metal complex ions. In some embodiments, potassium hydroxide is used.

In some embodiments, a combination of sodium hydroxide and potassium hydroxide is used. The sodium hydroxide interacts with the aluminium (where this is the multivalent metal) in the formation of complex ions. Potassium hydroxide is more commonly used in latex compositions, and the presence of potassium hydroxide as one of the alkalis assists in avoiding potential localised coagulation when the cross-linking agent is added to the aqueous suspension of synthetic carboxylated polymer. The relative amount of sodium hydroxide to potassium hydroxide may be about 3:1 to 1:3. The amount may be about 2:1 (sodium to potassium) or about 1:1.

Where a solubilised multivalent metal-based cross-linking agent is used as the or one of the cross-linking agents, the pH must be such that solubilisation of the multivalent metal is achieved, through production of negatively charged multivalent metal complex ions. In embodiments, the pH is "matched" to the pH of the aqueous suspension of synthetic film-forming polymer. In general terms, the pH should be high enough to achieve solubilisation of the multivalent metal. This may be between 9.0 and 13.5, such as between 9.0 and 13.0, 9.0 and 12.5, 9.0 and 12, between 9.0 and 11.5, such as between 9.0 and 11.0, 9.2 and 11.0, 9.5 and 11.0, 9.5 and 10.5, 9.8 and 10.8, 10.0 and 11.0, or 10.0 and 10.8. When a salt form of the multivalent metal is used, it is preferred to use a higher pH to subdue the acidic properties, so a pH of around 10.0-13.0 may be desired, such as between about 11.5 and 12.5, or about 12.

In addition to influencing the pH of the cross-linking composition, the alkali has an influence on the stability of the complex ions in solution. Sodium from sodium oxide stabilises the complex ions in solution, and produces sodium hydroxide (an alkali hydroxide) in solution. Higher amounts of sodium hydroxide allow for greater activation of the multivalent metal (e.g. aluminium) in the complex, and allows for a reduced amount of multivalent metal source to be used in the composition.

Mechanical Stabiliser in the Cross-Linking Composition

When using a solubilised multivalent metal as one of the cross-linking agents, it is advantageous to include in the cross-linking composition a mechanical stabiliser for mechanically (i.e. structurally) maintaining the negatively-charged multivalent metal complex ions in solution. The mechanical stabiliser aids in maintaining the stability of the solution, by providing structural support around the complex ions to avoid re-precipitation or re-crystallisation. The mechanical stabiliser may be any agent that has this function. The mechanical stabiliser may be a water-miscible or water-soluble organic polyol, or a water-soluble or water-miscible thickening agent, examples of which are well known in food or pharmaceutical manufacture. Examples of such polyols and thickeners include glycerine, sugars and sugar alcohols, maltodextrin, polysaccharide, polyglycerol, starch, modified starch, and mixtures thereof.

The cross-linking composition is suitably free of polyethylene glycol, or contains only an amount of polyethylene glycol that is insufficient for it to function as a chain extender. The amount is suitably less than 0.5 phr, or less than 0.4, 0.3, 0.2, 0.1 or less than 0.05 phr. It has been postulated in the art that polyethylene glycol functions as a chain extender. Such a chain-extender is not required in the present formulation, and preferably avoided.

The latex composition is also suitably free of polyethylene oxide, or contains less than 0.3, less than 0.2 or less than 0.1 phr polyethylene oxide. Such agents are indicated to be required in the prior art to achieve a low modulus. Polyethylene oxide is not an essential component of the present formulation for the production of thin film gloves with a modulus greater than 6.5 MPa.

Amounts of Components in the Cross-Linking Composition

The amount of (A) multimetal oxide, (B) multivalent metal hydroxide or (C) multivalent metal salt in the latex composition may be anywhere between 0.01-5 phr across the range of embodiments described herein. Although that is the case, in particular embodiments, the phr amounts used may fall within a narrower range of values.

Whilst any amount within this range may be used, in particular embodiments a low amount of (A) multimetal oxide, (B) multivalent metal hydroxide or (C) multivalent metal salt is incorporated into the composition. The amount may be within the range of 0.01-0.5 phr. In particular embodiments, the amount of multivalent metal ion is not more than 0.4 phr, or not more than 0.35 phr. The maximum amount may be not more than 0.35, 0.34, 0.33, 0.32, 0.31, 0.30, 0.29, 0.28, 0.27, 0.26 or 0.25. The minimum amount may be at least 0.05, 0.06, 0.07, 0.08, 0.09, 0.1, 0.11, 0.12, 0.13, 0.14, 0.15, 0.16, 0.17, 0.18, 0.19, or 0.2 phr. Any maximum and minimum value may be combined to form a range. Using low levels of the multivalent metal source in the cross-linking composition produces gloves having excellent properties, with low reagent utilisation, as demonstrated in various examples in this specification.

In other embodiments, the amount may be within the broader range of 0.01-5.0 phr, or 0.01-1.0 phr, including ranges up to 0.9, 0.8, 0.7, 0.6, 0.5 phr. These maximums may be combined with any minimum indicated in the preceding paragraph. In some embodiments, the amount of multi metal oxide used could be at the higher end of the range. For example, the amount of multi metal oxide as the source for the cross-linking agent could be within one of the following ranges: 0.15 to 5 phr, 1.0 to 5 phr, 2.0 to 4.0 phr, 2.5 to 5 phr or 3.0 to 5.0 phr. In other embodiments, for example, where the degree of carboxylation is low, or there is a high percentage of other polymers that undergo covalent cross-linking (or are self-crosslinkable), the amount of could be lower. Suitable ranges include 0.01-1.0, 0.01-0.8, 0.01-0.6, 0.01-0.5, 0.01-0.4, 0.01-0.3 or 0.01-0.2. These amounts have been determined using the example of sodium aluminate as the source. To determine the corresponding phr ranges for other agents, the appropriate conversions can be calculated.

Preparation of a Cross-Linking Composition

A cross-linking composition can be formed by solubilising a multimetal oxide of the multivalent metal, a hydroxide of the multivalent metal or a salt of the multivalent metal in water, and controlling the pH to be at least 9.0. Heating may be useful, or necessary, for solubilisation. The forming of the cross-linking composition may further include the step of dissolving alkali in hydroxide form in the cross-linking composition. The hydroxide may be added and dissolved into the solution prior to, at the same time as, or following the solubilisation of the multimetal oxide of the multivalent metal, hydroxide of the multivalent metal or salt of the multivalent metal.

In some instances, heating can be avoided. However, heating can assist to maximise dissolution. The heating may be to a temperature of at least 35° C., at least 40° C., at least 50° C., at least 80° C. or around 95° C. to boiling. Control of the pH is typically achieved through addition of alkali (e.g. alkali hydroxide), as described above, to raise the pH to at least 9.0 (to the specific level set or targeted for the process). The pH may alternatively be adjusted for pH stabilisation at a target pH level. Control of the pH may otherwise be achieved through the use of a multimetal source that has a high pH. Nevertheless, even if the pH is above the required level, it is usually necessary to add further alkali to control the pH more precisely, to allow matching of the pH to that of the aqueous suspension of the synthetic carboxylated polymer. Further, as described above, having a combination of sodium and potassium hydroxide provides advantages when the cross-linking composition and the aqueous suspension of the synthetic carboxylated polymer are combined.

When mechanical stabiliser is used, in accordance with preferred embodiments, the mechanical stabiliser is added to the cross-linking composition to maintain the multivalent metal complex ions in solution, to form a stabilised cross-linking composition, prior to addition of the cross-linking composition to the aqueous suspension of synthetic carboxylated polymer.

In addition to, or in place of, the mechanical stabiliser, a surfactant may be used to improve stability of the cross-linking composition. In embodiments, the surfactant is combined with the cross-linking composition prior to the composition being added to the latex for the purpose of maintaining a multivalent metal in the cross-linking composition in solution as a negatively charged multivalent metal complex ion. When a cross-linking composition is used, the cross-linking composition needs to be very stable to handle combination into the latex composition in a manner that suits the production of the articles described herein.

Initially, a relatively highly concentrated cross-linking composition can be prepared. Relative amounts of components used in the production of the concentrated cross-linking composition may be, per 100 parts by weight of water:

Between 0.01 and 5 parts of the (A) multimetal oxide of the multivalent metal, the (B) hydroxide of the multivalent metal or the (C) salt of the multivalent metal (preferably between 0.05 and 3 parts, or between 0.1 and 2 parts); and Between 0.01 and 5 parts of alkali in hydroxide form (preferably between 0.05 and 4 parts when using component (A) above, between 0.05 and 3 parts when using component (B) above, or between 0.05 and 4 parts when using component (C) above).

The concentrated composition may further comprise:

Between 0.03 and 15 parts of stabiliser (i.e. total stabiliser, in the case of a mixture; preferably between 0.5 and 3 parts).

There may however be some variation in the amounts shown above—these are indicative values that have been shown to work effectively.

After forming of the concentrated composition, this may be diluted prior to addition of the cross-linking composition to the aqueous suspension of the synthetic polymer. The dilution is usually performed to reduce the concentration such that the multivalent metal ion concentration is reduced to between 0.33-3.3% by weight of the cross-linking composition. In this case, the amount is based on the metal ion, rather than the total weight of the source of multivalent metal ions (A), (B) or (C). If considering the amount of the multivalent metal source (i.e. (A), (B) or (C)) in the diluted cross-linking composition, the diluted concentration of the source is typically between 1-10% by weight of the cross-linking composition. As one example, the diluted concentration of sodium aluminate in the cross-linking composition may be about 5% (about 1.5% aluminium). The initial concentration of multivalent metal ions based on the above typical amounts in the concentrated cross-linking composition is around 3 to 10% by weight.

Consequently, the cross-linking composition (in a form ready for combination with the latex) may comprise, per 100 parts by weight of water:
- Between 0.0001 and 0.5 parts of the multivalent metal source (A), (B) or (C) (e.g. between 0.0005 and 0.3 parts or 0.001 and 0.2 parts of one of those components); and
- Between 0.0001 and 0.5 parts of alkali hydroxide (preferably between 0.001 and 0.4 parts, between 0.005 and 0.3 parts, or between 0.005 and 0.4 parts).

The cross-linking composition (in a form ready for combination with the latex) may further comprise:
- Between 0.0003 and 1.5 parts of stabiliser (i.e. total stabiliser; preferably between 0.0005 and 0.3 parts).

Second Cross-Linking Agent

When a cross-linking composition containing solubilised multivalent metal is used, additional cross-linking agent (which may be referred to as a "second cross-linking agent") can be used. In other embodiments, the cross-linking agent does not contain the solubilised multivalent metal, and instead the cross-linking agent comprises one or more of a solid metal oxide, sulphur and sulphur donor cross-linking agents.

In this section, embodiments based on a combination of the cross-linking composition and one or more "second cross-linking agents" are described. The second cross-linking agent is typically added as a separate component during the formation of the latex composition, and in solid form. The solid particulate cross-linking agents may be added to the aqueous suspension of the synthetic polymer at the same time as the cross-linking composition, or following addition of the cross-linking composition.

The second cross-linking agent can be selected from any of the covalent cross-linking agents, ionic cross-linking agents, and combinations thereof listed above. In some embodiments, the second cross-linking agent comprises sulphur, a sulphur donor, and metal oxide.

In some embodiments, the second cross-linking agent may be selected from either:
- sulphur and a sulphur donor,
- a multivalent metal oxide or ionic cross-linking agent (e.g. a solid ionic cross-linking agent),
- sulphur, a sulphur donor and an ionic cross-linking agent, or
- a sulphur donor.

The solid ionic cross-linking agent class includes such as zinc oxide and magnesium oxide. These are typically milled to a fine particle size prior to incorporation into the composition. Preferably, the average particle size is below 5 microns. Uniform particle size is desirable, and coarse milling may result in non-uniform particles and therefore a non-uniform film, which can result in high fluctuation in film properties.

Amounts of Second Cross-Linkers

In broad terms, any amount of second cross-linker may be used, as required for the final article properties. Thus, the total amount of cross-linking agents in the composition (including that added in the formation of the cross-linking composition) may be between 0.01 and 14 phr. However, it is desirable to minimise cross-linker amounts. With the use of the cross-linking composition of the present invention, this is possible. The total cross-linking agent amount (including that used to form the cross-linking composition) may be within one of the following ranges: 0.01-14.5 phr, 0.2-12.5 phr, 0.3-10 phr, 0.1-10 phr, 0.2-10 phr, 0.3-9 phr, 0.5-9 phr, 0.8-9 phr, 0.3-8 phr, 0.5-8 phr, 0.8-6 phr, 1-5 phr, 2-9 phr, 3-10 phr, 3-7 phr, 1-3 phr, 0.01-0.5 phr, 0.01-1.0 phr.

In desirable embodiments, the amount of each secondary cross-linker is preferably not more than 1.0 phr, preferably not more than 0.9, 0.8. 0.7, 0.6, 0.5, 0.4, 0.3 or 0.2 phr. The total amount of all secondary cross-linkers is preferably also not more than (or is below) 1.0, 0.9, 0.8. 0.7, 0.6, or 0.5 phr.

The amount of sulphur, when used as a second cross-linker, may be between 0.0-5.5 phr or 0.01-5.5 phr. The amount may be lower still, at 0.0-3.5 phr, such as 0.01-3.0 phr, 0.01-2.0 phr, 0.01-1.5 phr, 0.01-1.0 phr or 0.01-0.5 phr. The amount is preferably not more than 1.0 phr, preferably not more than 0.9, 0.8. 0.7, 0.6, 0.5, 0.4, 0.3 or 0.2 phr.

The amount of sulphur donor, when used as a second cross-linker, may be between 0.0-2.0 phr, such as between 0.01-2.0 phr, 0.01-1.5 phr, 0.01-1.0 phr, 0.1-1.5 phr, 0.1-1.0 phr, 0.2-1.0 phr, 0.3-2.0 phr, 0.3-1.5 phr or 0.2-0.6 phr. The amount is preferably not more than 1.0 phr, preferably not more than 0.9, 0.8. 0.7, 0.6, 0.5, 0.4, 0.3 or 0.2 phr.

The amount of organic cross-linking agent, when used as a second cross-linker, may be between 0.0-4.0 phr, such as 0.01-4.0. The amount may be lower still, at 0.01-3.0 phr, or 0.01-2.0 phr, or 0.01-1.0 phr.

The amount of ionic cross-linking agent, when used as a second cross-linker, may be between 0.0-4.0 phr, such as 0.01-4.0. The amount is preferably lower still, at 0.01-3.0 phr, or 0.01-2.0 phr, 0.01-1.0 phr or 0.01-0.5 phr. This applies to solid multivalent metal oxides such as zinc oxide. The amount is preferably not more than 1.0 phr, preferably not more than 0.9, 0.8. 0.7, 0.6, 0.5, 0.4, 0.3 or 0.2 phr.

The cross-linking agents preferably consist essentially of one or more of a solubilised trivalent metal compound, a divalent metal oxide, sulphur and a sulphur donor, or a combination thereof. The cross-linking agent is therefore preferably free of organic cross-linking agents, such as polyethylene glycol cross-linker.

Combining Components of the Elastomeric Film-Forming Composition

When a solubilised multivalent metal is used as one of the cross-linking agents (such as solubilised sodium aluminate), the best results are obtained when a shock-increase in the pH of the latex composition (i.e. the aqueous suspension of the synthetic polymer, as it is combined with other components to produce the latex composition) is avoided. This can be achieved in two ways. One way involves very slow addition of the cross-linking composition to the aqueous suspension of the synthetic polymer, to allow for equilibration of the pH without a shock increase in pH. (It is noted that the higher the pH and concentration of the cross-linking composition, the slower the addition rate, and vice versa.) The second alternative is to ensure that the pH of the cross-linking composition is reasonably "matched" to the pH of aqueous suspension of the synthetic carboxylated polymer. If the pH's are not too far apart, then the rate of addition is not as critical. Ideally, the matching involves bringing the pH of both components (or streams) within 1.0 units, or between 0.5 units of each other, preferably within 0.2 units of each other, and most preferably the same pH. However, as noted above, an even higher pH difference is permissible if there is very slow addition if the cross-linking composition stream, and the cross-linking composition added is suitably stabilised with mechanical stabiliser and/or surfactant. By adding the cross-linking composition as a diluted stream (i.e. water making up more than 90% of the cross-linking composition, such about 90% or more, about 91% or more, about 92% or more, about 93% or more, about 94% or more, or about 95% or more), at a slow rate of addition and/or with a matched pH, it is possible to produce a latex composition from which there is no, or minimal, precipitation of the multivalent metal. (That is, there is less than 20%, less than 15%, less than 10%, less than 5%, less than 2% and preferably no precipitation of the multivalent metal from the latex composition).

Supply of an aqueous suspension of a synthetic polymer to a manufacturing facility is usually performed in the form of a concentrated solution, with a pH below 9.0. In the method of the invention, it may be necessary to add alkali to the aqueous suspension of the synthetic polymer prior to the addition of the cross-linking composition to raise the pH of the aqueous suspension to at least 9.0. Alkali is referred to below in the list of other components that may be present in the latex composition, as a stabiliser. The amount should be controlled to ensure the required pH for the aqueous suspension.

It may also be necessary to dilute the supplied aqueous suspension of synthetic carboxylated polymer to a total solids content (TSC) that is closer to that required in the production of the elastomeric gloves. For the production of the present low-weight gloves, the final dipping TSC is about 3% to 15%. In some embodiments, the final dipping TSC is about 3% to 12%, 4% to 15%, 3% to 11%, 4% to 14%, 4% to 13%, 4% to 12%, 4% to 11%, 4% to 10%, 3% to 10%, 5% to 14%, 5% to 13%, 5% to 12%, 5% to 11%, 5% to 10%, preferably from 3% to 12%. The initial dilution will be to a TSC that is a little higher than the final dipping TSC concentration. The supplied aqueous suspension of synthetic carboxylated polymer TSC typically needs to be at least about 3% or 5% higher than the TSC at which dipping is performed, in view of the fact that the composition will be diluted through the addition of the aqueous form of cross-linking composition of the present invention. Supplied latex may be provided at a TSC of around 45%, around 50%, around 55% or around 60%, in some examples.

In one embodiment, there is provided a synthetic latex composition comprising a synthetic polymer and a cross-linking agent, wherein the cross-linking agent is present in an amount of less than 1.0 phr and the total solids content of the composition is from about 3% to about 15%.

Adding of the Cross-Linking Composition to the Polymer Suspension

The cross-linking composition may be added to the aqueous suspension of the polymer in an amount of between about 0.01 and 0.5 parts per 100 parts by volume of the aqueous suspension of the synthetic carboxylated polymer. The cross-linking composition is very dilute, so a relatively high volume of dilute cross-linking composition is required. This is another factor found to aid in the formation of a stable latex composition. The typical amount is amount in some embodiments is between 0.03 and 0.3 parts (per 100 parts synthetic polymer suspension), and in some cases between 0.03 and 0.1 parts.

Prior to, or at the same time that the cross-linking composition is added, it is advantageous to add surfactant to the aqueous suspension of synthetic carboxylated polymer. This aids to maintain the stability of the emulsion and the stability of the multivalent metal complex ions in solution. Such surfactants are additional to those that may be used in the formation of the cross-linking composition, which may also be selected from the examples set out below.

The surfactant may be selected from anionic surfactants, non-ionic surfactants, and combinations of agents from one or both classes.

Suitable anionic surfactants include, but are not limited to, ($C_8$-$C_{18}$) alkyl sulfates, ($C_8$-$C_{18}$) linear alkyl aryl sulfates, ($C_8$-$C_{18}$) alkyl ether sulfates, ($C_8$-$C_{18}$) fatty acid salts, ($C_8$-$C_{18}$) alkyl ether sulfates having one or more moles of ethoxylation, ($C_8$-$C_{18}$) alkyl ether sulfonates, sulfate esters of an alkylphenoxy polyoxyethylene ethanol, ($C_8$-$C_{18}$) alkamine oxides, ($C_8$-$C_{18}$) alkoyl sarcosinates, ($C_8$-$C_{18}$) sulfoacetates, ($C_8$-$C_{18}$) sulfosuccinates, ($C_8$-$C_{18}$) alkyl diphenyl oxide disulfonates, methyl ester sulfonates, alpha-olefin sulfonates, alkyl carbonates, alkyl ether carboxylates, fatty acids, sarcosinates, octoxynol or nonoxynol phosphates, taurates, fatty taurides, fatty acid amide polyoxyethylene sulfates, isethionates and or blends thereof. ($C_8$-$C_{18}$) alkyl group may be straight chain (e.g., stearic, cetyl, lauric, oleic, myristic) or branched (e.g. 2-ethylhexyl). The cation of the anionic surfactant may be an alkali metal (e.g., sodium or potassium), ammonium, $C_1$-$C_4$ alkylammonium (e.g., mono-, di-, tri-), or $C_1$-$C_3$ alkanolammonium (e.g., mono-, di-, tri-). The specific examples of such anionic surfactants include, but are not limited to, lauryl sulfates, octyl sulfates, 2-ethylhexyl sulfates, dodecyl benzene sulfonates, lauramine oxide, decyl sulfates, tridecyl sulfates, cocoates, lauryl sarcosinates, lauryl sulfosuccinates, lauryl ether sulfates (one or more ethylene oxides), myristyl sulfates, oleates, stearates, tallates, ricinoleates, cetyl sulfates and so forth.

Non-ionic surfactants include the following non-exhaustive examples: ethoxylated alkylphenols, ethoxylated and propoxylated fatty alcohols, polyethylene glycol ethers of methyl glucose, polyethylene glycol ethers of sorbitol, ethylene oxide-propylene oxide block copolymers, ethoxylated esters of fatty ($C_8$-$C_{18}$) acids, condensation products of ethylene oxide with long chain amines or amides, condensation products of ethylene oxide with alcohols, and blend thereof. Specific examples, but are not limited to, methyl gluceth-10, PEG-20 methyl glucose distearate, PEG-20 methyl glucose sesquistearate, $C_{11-15}$ pareth-20, ceteth-8, ceteth-12, dodxynol-12, laureth-15, PEG-20 castor oil, pollysorbate-20, steareth-20, polyoxyethylene-10 cetyl ether, polyoxyethylene-10 oleyl ether, polyoxyethylene-20 oleyl ether, an ethoxylated nonylphenol, ethoxylated octylphenol, ethoxylated dodecylphenol, or ethoxylated fatty ($C_6$-$C_{22}$) alcohol, including 3 to 20 ethylene oxide moieties, polyoxyethylene-20 isohexadecyl ether, polyoxyethylene-23 glycerol laurate, polyoxyethylene-20 glyceryl stearate, PPG-10 methyl glucose ether, PPG-20 methyl glucose ether, polyoxyethylene-20 sorbitan monoesters, polyoxyethylene-80 castor oil, polyoxyethylene-15 tridecyl ether, polyoxyethylene-6 tridecyl ether, laureth-2, laureth-3, laureth-4, PEG-3 castor oil, PEG 600 dioleate, PEG 400 dioleate, oxyethanol, 2,6,8-trimethyl-4-nonyloxypolyethyleneoxyethanol, alkyleneoxypolyethylene-oxyethanol, alkyleneoxypolyethyleneoxyethanol water soluble alcohol ethylene oxide condensates with $C_8$-$C_{18}$ carbon atoms in a straight or branched chain configuration with 5 to 30 moles of ethylene oxide and blends thereof. Other suitable nonionic surfactants include the polyethylene oxide condensates of one more of alkyl phenol containing $C_8$-$C_{18}$ carbon atoms in a straight or branched chain configuration with 5 to 30 moles of ethylene oxide and blends thereof. Specific examples of alkyl phenol ethoxylates include nonyl condensed with about 7-13/9.5 moles of ethylene oxide per mole of octyl/nonyl phenol, dinonyl phenol condensed with about 12/15 moles of EO (ethylene oxide) per mole of phenol and mixtures thereof.

The surfactant is typically added as an aqueous solution. The solution concentration is typically around 2-10%. The amount of surfactant solution that may be added to the aqueous suspension of the polymer with the cross-linking composition may be such as to provide 0.01-5 phr to the latex composition. The range may be between 0.1-2 phr, or about 0.6 phr. It is noted that this surfactant is additional to any surfactant that may be present in the concentrated aqueous suspension of synthetic carboxylated polymer supplied by the supplier.

Other Components of the Elastomeric Film-Forming Composition

Other components may be added to the latex composition to form the elastomeric film-forming composition. These other components may include components selected from the group consisting of plasticizers, anti-ozonants, stabilisers such as pH stabilisers, emulsifiers, antioxidants, vulcanising agents, polymerisation initiators, pigments, fillers, colourising agents and sensitisers. Many of these agents are added in particulate form. Others are added as liquids. These are added prior to forming the latex composition into the shape of the synthetic elastomeric article.

Stabilisers may be used in the elastomeric film-forming composition. The stabilizer may be, for example, an anionic surfactant and/or a non-ionic surfactant. The elastomer-forming polymer can be diluted with a solution of a stabilizer, such as potassium hydroxide, ammonium hydroxide and/or sodium hydroxide. The amount of stabiliser used is dependent on the polymer used in the elastomeric film-forming composition, the pH of the composition and other factors. The stabiliser can range from 0.1-5.0 phr, e.g. 0.5 to 2 phr, preferably 1.0 to 1.5 phr, which is diluted with water, preferably filtered water—or de-ionized water, or water having a total solid content of around 5 ppm level.

Emulsifiers may be used in the elastomeric film-forming composition. Suitable emulsifiers include comprise sodium alkyl aryl sulphates, sodium alkyl sulphates or other anionic/non-ionic surfactants. The amount of emulsifier used is dependent on the on the polymer used in the elastomeric film-forming composition, the pH of the composition and other factors. The amount of emulsifier can range from about 0.1 to 3 phr.

pH stabilisers may be used to avoid the possibility of destabilization, which is possible where the polymer contains carboxylic acid groups. Suitable pH stabilisers include alkali hydroxides such as potassium hydroxide, ammonium hydroxide and/or sodium hydroxide. Preferably, the pH stabiliser is potassium hydroxide. A diluted stabilizer solution can be mixed with the polymer. The pH of the mixture is suitably adjusted to between about 8.5 to about 12.5, or between about 8.5 to about 11.0. The cross-linking agent(s) can then be added to the mixture.

Anti-ozonants may be used in the elastomeric film-forming composition. Suitable anti-ozonants include paraffinic waxes, microcrystalline waxes and intermediate types (which are blends of both paraffinic and microcrystalline waxes). The amount of anti-ozonant can range from about 0.0 to 5.0 phr.

Antioxidants may be added to the elastomeric film-forming composition of the present invention. Suitable antioxidants include hindered arylamines or polymeric hindered phenols, and Wingstay L (the product of p-cresol and dicyclopentadiene). The antioxidant may, for example, be added in an amount ranging from 0.0-5.0 phr, 0.0-3.0 phr, 0.0-1.0 phr or 0.3-0.5 phr.

Pigments such as titanium dioxide, selected for its pigmentation, to reduce the transparency of the final elastomeric film, may be added in amounts ranging from 0.01-10.0 phr, such as 1.5-2.0 phr or 1.0-3.0 phr and colorants can also be added in the desired amounts. The mixture is then diluted to the target total solids concentration by the addition of a liquid, such as water. The pigments used in the elastomeric film-forming composition may be selected from the group consisting of EN/USFDA approved dyes.

Rubber reoderants may be used in the elastomeric film-forming composition. Suitable rubber reoderants include perfume oils of natural or synthetic origins. The amount of rubber reoderant can range from about 0.001 to 2.0 phr.

Wetting agents may be used in the elastomeric film-forming composition. Suitable wetting agent emulsifiers include anionic surfactants like sodium dodecyl benzene sulfonate or sodium lauryl ether sulfate, or non-ionic ethoxylated alkyl phenols such as octylphenoxy polyethoxy ethanol or other non-ionic wetting agents. The amount of wetting agent can range from about 0.001 to 2.0 phr.

Defoamers may be used in the elastomeric film-forming composition. Defoamers may be chosen from naphthalene type defoamers, silicone type defoamers and other non hydrocarbon type defoamers or defoamers of refined oil of vegetable origin. The amount of defoamers can range from about 0.001 to 2.0 phr.

The elastomeric film-forming composition could also be blended with inorganic filler. Suitable inorganic fillers include titanium calcium carbonate, carbon black or clay. Preferably, the amount of inorganic filler included in the blend would not exceed 75% either alone or in combination. It will be appreciated that the blended composition will retain the favorable properties.

Sensitisers are chemicals that can be used in compositions for producing elastomeric films to control the amount of the composition that will remain coated on the mould during dipping (film deposition). Examples of sensitisers known in the art that can be used in the composition for producing an elastomeric film include polyvinyl methyl ether, polypropylene glycol, ammonium nitrate and ammonium chloride. The amount is generally be between 0.01 to 2.0 phr, e.g. 0.1 to 1.0 phr. When other techniques are used for controlling the film thickness on the mould, such as the use of pre-dipping the mould into coagulant before undertaking the multiple dipping into the composition for producing the elastomeric film, the composition for producing an elastomeric film may not require a sensitiser.

Those skilled in the art will readily be able to vary the components of the elastomeric glove or film-forming composition to suit the circumstances. It will also be understood by those of skill in the art that specific chemicals or compounds which have been listed above are intended to be representative of conventional materials that may be used in formulating the elastomeric film-forming composition and are merely intended as non-limiting examples of each such component of the composition. Nevertheless, it is preferred to utilize the compositions and guidance provided herein, since these have been found to be optimal in achieving the production of the claimed thin film gloves with acceptable performance properties.

It is noted that a number of the components of the latex composition are particulate, and it is preferred to ensure that the particle size is sufficiently low to allow for the casting of an ultra-thin film on the surface of the mould. As indicated above, a solubilised cross-linking composition may be used as the (or one of the) cross-linking agents. Using a solubilised form of a cross-linking agent in the composition has been found to be preferred for the production of ultra-thin films, since it reduces or minimises the number of particulate components that would otherwise enlarge the thickness of the film through overlaying of the particles in a particle-dense composition. To achieve the desired elastomeric properties, it is further useful to include a secondary cross-linking agent (or combination thereof), in addition to the solubilised cross-linking composition. The most useful secondary cross-linking agents are typically in solid form, with varying particle size. Some secondary cross-linking agents may be used in solubilised form (e.g. sulphur may be solubilised). In the present application, it is desirable for the solid secondary cross-linking agents to be used at a particle size of less than 5 µm (i.e. at least 95% of the particles are less than 5 µm in size). It is also desirable for any other solid components that are not dissolved in the latex composition to have a low particle size. Further, it is desirable to control the number of particles (measured by total particulate cross-linker phr) to a relatively low level. These factors allow for the formation of a thin film product, with the avoidance of excessive accumulation of cross-linker particles on top of each other in the film that is cast on the mould.

The elastomeric film-forming composition is preferably formalin-free.

Final Composition Preparation Stages

All components of the elastomeric film-forming composition are combined as described above, taking care, where necessary, to avoid pH shock which would cause coagulation.

After mixing of all components, the elastomeric film-forming composition is then left for maturation. The length of maturation may vary depending on the amount of cross-linking agent and the degree of carboxylation of the polymer, where the polymer is carboxylated. The composition may be left for a minimum of 2 to 18 hours for the purpose of removing air bubbles inside the compounded polymer. The compounded elastomeric film-forming composition with suitable additives could be prematured by holding the composition at a controlled elevated temperature. For example, the elastomeric film-forming composition could be held at 40° C. to 60° C. for a period of, for example, about 4 hours to about 24 hours depending on the temperature, degree of carboxylation of the polymer, the amount and type of vulcanization activators and Sulphur donors, and type and quantity of pH stabilizer and emulsifier stabilizer and wetting agents/surfactants.

Preparation of Elastomeric Articles, Such as Films

The composition is formed into the shape of a glove, and then cured. Curing is used in a general sense, to refer to the stage during which cross-linking is performed.

The forming of the product into the desired shape suitably involves dipping a glove-shaped former (which may alternatively be referred to as a mould) into the composition. The former may be of any type known in the art. In some embodiments, the former is of one of the new classes described in detail below.

The steps in the manufacture of the gloves are as generally described in PCT/AU2014/000726 and PCT/AU2014/000727. However, particular steps and conditions are used to control the formation of the gloves so as to have the very low thickness as required by the present application. In addition, the former design is also controlled so as to allow the formation of the ultra-thin gloves, as described below.

The process steps in some embodiments are as follows:

Step (a) Dipping the Former into a Coagulant Composition

A glove-shaped former is dipped into a preliminary composition, conventionally referred to as a coagulant composition. The coagulant composition typically contains multi-valent ions in solution. This procedure leaves a thin coating of the charged ions on the surface of the former. The charged ions coating assists in controlling the amount composition for forming the elastomeric film (the latex composition) that will subsequently remain on the surface of the mould after dipping into the latex composition, through charge interactions.

The concentration of multivalent ions in the coagulant can broadly be in the range of 0.0-20% by weight of the coagulant solution (measured as the compound of the multivalent ion in the solution of the multivalent ions), depending on the desired thickness of the elastomeric film layers and the number of layers to be applied (i.e. one layer or two or more layers). For preparation of thin layers, the concentration is suitably in the range of 0.0-20%, 0.0-15%, 0.1-20%, 0.0-12%, 0.1-12%, 0.1-10%, 0.1-5%, 0.5-12%, 0.5-10%, 0.5-5%, 1.5-20%, 1.5-15%, 1.0-10%, 1.5-10%, and 1-5%.

Cationic multivalent ion-containing coagulants are typically used, such as a calcium coagulant. The coagulant may be selected from calcium chloride, magnesium chloride, sodium chloride and other forms of monovalent and multivalent metal salts which exhibit a cationic ion upon dissolution, since the deposition of the film requires the presence of some positively charged ions in the solution.

It will be noted that the coagulant composition may contain a zero amount of coagulating multivalent ions. Gloves can be produced without any coagulant. Whilst that is the case, the glove former may still be dipped into a preliminary composition (which may be referred to as a coagulant composition regardless of the absence of coagulating multivalent ions) for the purpose of providing other useful properties, such as mould release properties. A heat sensitiser may be used in addition to, or in place of, a conventional coagulant.

The preliminary composition into which the former is dipped, conventionally referred to as the coagulant composition, may comprise a mould release agent. A mould release agent is an agent that aids in the release of the cured glove product from the former on stripping. The mould release agent is a particulate mould release agent. Examples of suitable mould release agents include stearate salts, such as alkali and alkaline earth metal stearates—viz. calcium stearate, magnesium stearate, zinc stearate, potassium stearate—polymeric mould release agents, silicone particulate materials and so forth. In preferred embodiments, the mould release agent is a stearate salt.

It is necessary to apply a mould release agent to the surface of the former prior to the latex dipping steps, and it is beneficial for the mould release agent to be a particulate mould release agent having an average particle size less than 15 µm. In some embodiments, it may be less than 14 µm, less than 13 µm, less than 12 µm, less than 11 µm or less than 10

µm. Such particle sizes refer to a D95 particle size (i.e. at least 95% of the particles are within this particle size range.)

The applicant postulated during performing their extensive test work that a significant amount of a mould release agent would be required to allow the very thin, relatively delicate, gloves to be stripped from the former. However, the applicant found that the use of high amounts of mould release agent to assist in stripping (slipping) the cured glove product off the mould adversely impacted on the article properties, including the uniformity of the glove thickness, which lead to areas of weakness and hence breakage on attempted stripping. The application of a higher amount of mould release agent also impacted on the colour of the final product. That is, the most commonly used mould release agents are dark in colour, and while this can be obscured in thicker gloves, ultra-thin gloves do not contain enough bulk to lessen the darkening effect of the mould release agent. The products produced with a high amount of mould release agent had an undesirable greyed appearance.

The applicant tried to avoid the use of a mould release agent, to avoid these challenges, but found it not possible to take this step without significantly impacting on the cost of production and generating other undesirable qualities in the glove products.

Ultimately, if the particle size of the mould release agent is minimised (i.e. it is brought within one of the size range indicated above), and at the same time the surface roughness of the former is controlled to be within a particular range, a suitable balance in properties is provided that enables the production of good quality, ultra-thin gloves, using conventional glove production lines (with conventional glove production speeds).

In terms of the former surface, modified formers were produced having a controlled surface roughness ($S_z$) within the range of 28 to 42 µm. The surface roughness was carefully controlled to be sufficient to allow pick-up of the latex composition (without dripping/pooling off the former), and to achieve the formation of a sufficiently uniform latex film layer on the former. Combining this with the particle size of the mould release agent in the coagulant also contributes to the production of a strong film with fewer defects. Larger mould release particles can change the surface of the coagulant-dipped former, and create areas of quasi-roughness that reduces the film thickness where such mould release agent particles have accumulated.

The surface roughness of the former used in the production of the gloves in accordance with preferred embodiments is described in detail below.

The coagulant composition may comprise any other additional agents as desired. Examples include surfactants, thickeners and anti-foaming agents. Thickeners may be cellulose-based thickeners or otherwise.

Typical amounts of components in the coagulant suited for use in the present application are as follows:

Coagulant ions—0 to 20% by weight (e.g. calcium-based coagulant)
Mould release agent—0.1 to 5.0% by weight (e.g. stearate)
Surfactant—0 to 1.0%, such as 0.001 to 1.0% by weight
Thickener—0 to 1.0%, such as 0.01-1.0% by weight
Anti-forming agent—0.001 to 1.0% by weight.

The time period over which the mould is lowered into the coagulant may be between 1 and 30 seconds, such as 2-30 seconds, 1-10 seconds, or 1-5 seconds. Then, the duration or dwell time for the mould in the coagulant is suitably between 0 and 50 seconds, such as between 1 and 50 seconds or between 1 and 30 seconds. In some embodiments, the dwell time for the mould in the coagulant is 1 to 10 seconds. In some embodiments, the dwell time for the mould in the coagulant may be longer than 30 seconds. The time period over which the mould is removed from the coagulant may be between 1 and 30 seconds, such as between 3 and 30 seconds or between 1 and 10 seconds. The total time period may, in one embodiment, be between 10-24 seconds. The temperature of the coagulant into which the mould is dipped may, for example, be between 30° C.-80° C.

It is noted that, in the context of dipping into coagulant or latex (see below), the time period for lowering ("in") covers the time from when the mould first touches the coagulant or latex composition until complete immersion (i.e. the lowest point to which the mould is lowered during immersion). The time period of removal or raising ("out") covers the time from the commencement of raising of the mould until the point at which the mould is completely removed from the coagulant or latex, and just breaks contact with the coagulant/latex surface.

It is also noted that the time periods indicated herein for dipping times are dependent on the speed of the production of line for glove production, and the size of the tanks present in the production line. These dipping time periods suit about 3.3 to 8 metres of effective length of coagulant and a linear speed of 20 metres/minute, which is a conventional line speed for thin film glove production. The latex dipping times indicated below suit 5-8 metres of effective length of latex at the same linear speed. Adjustments can be made for production lines with different tank lengths, and different linear speeds.

Step (b) Drying or Partially Drying the Dipped Former

After the dipping of step (a), former is dried or partially dried.

Step (i) Dipping the Former into the Elastomeric Film-Forming Composition to Produce a Layer of Elastomeric Article-Forming Composition on the Mould The former is dipped into the composition for producing an elastomeric film (i.e. the latex composition), which contains the components as described in detail above. The duration of dipping, temperature, and former surface temperature may be as described in the PCT publications referred to above. The duration of dipping, or the dwell time refers to the time taken from the point at which the glove former is completely immersed into the composition, until the point at which the glove former commences being removed from the composition.

The former is in the dipping tank for an amount of time to ensure the former is evenly coated, but not so long as to develop a thicker coating than necessary. The time period over which the mould is lowered into the dipping tank or latex composition may be between 1 and 30 seconds, such as 2-30 seconds, 1-10 seconds, or 1 to 5 seconds. Then, depending on the required thickness of the coating, the dwell time of the former in the dipping tank may be between about 0-50 seconds, such as between about 1-50 seconds, 0-15 seconds, 1 to 15 seconds, 2 to 15 seconds, 0 to 10 seconds, 1 to 10 seconds, 5 to 20 seconds, 10 to 30 seconds, 15 to 25 seconds, 20 to 40 seconds, 25-40 seconds, 30 to 40 seconds or 20 to 50 seconds. The time period over which the mould is removed from the latex may be between 1 and 30 seconds, such as 3-30 seconds, 1-30 seconds or 1-20 seconds. In some embodiments, the total time period may be between about 3 to 50 seconds, such as 5 to 30 seconds. The time period may be 15-24 seconds in some embodiments.

The temperature of the composition into which the former is dipped is generally within the range of 10° C. to 60° C., such as 10° C. to 50° C., 15° C. to 50° C., 20° C. to 50° C., 25° C. to 50° C., 25° C. to 45° C., 20° C. to 40° C. or 20° C. to 35° C. Preferably, the composition into which the former is dipped is constantly cooled with chilled water and the latex bath temperature is kept between 20-35° C., such as 20° C. to 30° C. and more preferably at 25° C. In some embodiments, the composition is constantly circulated in the tank to avoid creaming and settling of the chemicals contained in the elastomeric film-forming composition.

Preferably, the surface temperature of the former does not exceed the temperature of the elastomeric film-forming composition by more than 80° C. It has been found by the applicant that if the surface temperature of the former is more than 80° C. higher than the temperature of the composition for producing an elastomeric film, shrinkage of the coating of elastomeric film-forming composition on the former may occur. In some embodiments, the surface temperature of the former is lower than the temperature of the elastomeric film-forming composition. However, typically, the surface temperature of the former is about 20° C. to 60° C. higher than the temperature of the elastomeric film-forming composition.

If a single film-layer glove is produced, the next step performed is step (v).

Step (ii) Optional Step of Drying or Partially Drying the Layer of Elastomeric Film-Forming Composition on the Former—not Performed if a Single Film-Layer Glove If a second dip is performed, then the initial layer of elastomeric film-forming composition is dried or partially dried on the former. The time and temperature of the drying stage can be controlled as desired to ensure adhesion/intermingling of the second layer on the first layer.

Step (iii) Optional Step of Dipping the Former Coated with the Dried or Partially Dried Layer of Elastomeric Film-Forming Composition into the Elastomeric Film-Forming Composition to Produce a Further Layer of Elastomeric Film-Forming Composition on the Former This step is optional, and is present when multi-layer articles are produced. The conditions for the second dip may be the same as those for the first dip, or this dip may be performed at a different total solids content, and for a shorter dwell time.

The former is in the dipping tank for an amount of time to ensure the former is evenly coated, but not so long as to develop a thicker coating than necessary. The time period over which the mould is lowered into the dipping tank (into the latex composition) may be between 1 and 30 seconds, such as 2-30 seconds, 1-10 seconds, or 1 to 5 seconds. Then, depending on the required thickness of the coating, the dwell time of the former in the dipping tank may be between about 0 and 50 seconds, such as 1-50 seconds, 1-20 seconds, 0-15 seconds, 1 to 15 seconds, 2 to 15 seconds, 0-10 seconds, or 1 to 10 seconds. In some embodiments, the dwell time for the second dipping step may be shorter, such as between about 1-15 seconds, such as between about 1 to 10 seconds, or 1 to 5 seconds. The time period over which the mould is removed from the latex may be between 1 and 30 seconds, such as 3-30 seconds, 1-30 seconds or 1-20 seconds. In some embodiments, the total time period may be between about 3 to 50 seconds, such as 5 to 30 seconds.

The temperature of the composition into which the former is dipped to produce the further layer is generally within the range of 10° C. to 60° C., such as 10° C. to 50° C., 15° C. to 50° C., 20° C. to 50° C., 25° C. to 50° C., 25° C. to 45° C., 20° C. to 40° C. or 20° C. to 35° C. Preferably, the composition into which the former is dipped to produce the further layer is constantly cooled with chilled water and the latex bath temperature is kept between 20-35° C., such as 20° C. to 30° C. and more preferably at 25° C. In some embodiments, the composition is constantly circulated in the tank to avoid creaming and settling of the chemicals contained in the elastomeric film-forming composition.

Preferably, the surface temperature of the former does not exceed the temperature of the elastomeric film-forming composition by more than 80° C. It has been found by the applicant that if the surface temperature of the former is more than 80° C. higher than the temperature of the composition for producing an elastomeric film, shrinkage of the coating of elastomeric film-forming composition on the former may occur. In some embodiments, the surface temperature of the former is lower than the temperature of the elastomeric film-forming composition. However, typically, the surface temperature of the former is about 20° C. to 60° C. higher than the temperature of the elastomeric film-forming composition.

Step (iv) Optionally Repeating the Drying or Partial Drying Step (ii) and the Further Dipping Step (iii)

This step is optional, and is preferably not performed. This step produces three or more layers of film, following the formation of a second layer of film in optional step (iii).

Optional Additional Steps Prior to Drying and Curing

Further steps can be taken to fine-tune the manufacture of the elastomeric film or article. The details of these steps are as described in the PCT publications referred to above. In brief, the film or article can be leached to remove extractable components, there may be a coating material applied, beading/cuffing cab be performed and/or the product may be passed through a curing or vulcanizing oven to evaporate the water in the film and enable better cross linking.

Step (v) Drying and/or Curing the Layered Elastomeric Film on the Former

The elastomeric film layer produced by the dipping step(s) is dried and/or cured in accordance with conventional procedures. The details of this step are as described in the PCT publications referred to above.

Optional Additional Steps Following Drying and Curing

The optional steps that may take place following drying and/or curing can include one or more of cooling, chlorination, post-curing rinsing, polymer coating and additional drying steps. The cured film may also be cooled/chlorinated/neutralized—post-leached in hot water and optionally dipped in lubricant solution or any silicone/silicone free polymers to aid stripping and better donning. The details of these optional steps are as described in the PCT publications referred to above.

Step (vi) Stripping

The glove is stripped from the former at the conclusion of the formation process.

Stripping is conventionally performed using machine or automated stripping equipment. During machine stripping, gloves are removed from the former using techniques such as compressed air application, a combination of air and mechanical gearing, and mechanical stripping (which involves automation to simulate the human motion of pulling a glove from the cuff off the mould). Stripping by machine rather than hand, while more cost-effective, requires the glove to be sufficiently robust to withstand the stripping pressures applied by the machinery, and requires the glove to be readily "released" from the mould surface (to slip off or over the surface). In conventional thin glove manufacture, there may be a low degree of glove removal failure (i.e. a low percentage of gloves that are not completely removed from the formers), which are removed manually before the formers proceed to washing. In the case of ultra-thin glove manufacture, the above-described glove production techniques enable machine stripping equipment to be used, thus saving considerable cost. The rate of stripping failure is kept to a relatively low level, such that at least 90% of the gloves are successfully removed by machine stripping, and typically at least 92%, at 95%, at 98% or a higher percentage of the gloves are successfully removed.

In the production of other, higher-value, dipped products, other stripping techniques are also available, such as air/water jet stripping. Air jet stripping is not widely used in glove production.

Formers

Conventional formers may be used to produce the ultra-thin gloves, although the quality of the gloves and/or the defect rates may be adversely impacted by production on such formers. In some embodiments, a former of one of the classes specified above (i.e. the controlled roughness former and/or the cuff-banded former) is used as the former for producing the ultra-thin gloves. Such (new) formers may also be used in the production of elastomeric gloves more generally, including gloves of standard film thickness (including gloves with a palm thickness of at least 0.05 mm).

The glove-shaped former may comprise (i) a palm zone, (ii) a cuff zone, (iii) between finger zones and (iv) finger zones. The location and size of these zones is described below.

In preferred embodiments, the palm zone has a surface roughness ($S_z$) of between 28 and 42 μm. Preferably the cuff zone also has this surface roughness.

Where reference is made to a surface roughness, unless indicated otherwise, this should be read as a reference to maximum peak size ($S_z$). $S_z$ is suitably measured using an optical microscope, in a non-contact method of surface roughness measurement. $S_z$ is a measurement of the maximum profile height of an area, and is the sum of the largest peak height value and the largest pit depth value within a defined area, in μm. $S_z$ is the areal extension of $R_z$, which is a measurement of the maximum height profile of a curve along a 2D line, calculated as the sum of the maximum peak and maximum trough along the line length. $S_z$ is calculated automatically by suitable instrumentation, such as the Keyence VHX-6000 High Resolution Digital Microscope. The measurements are calculated in accordance with ISO 25178. The surface roughness in a particular zone of the former, or in the zone of the glove, is assessed by taking a surface roughness measurement at one location at or near the middle of that zone.

The $S_z$ of the former at the palm is preferably a minimum of 28, 29, 30, 31, or 32 μm. The $S_z$ of the former at the palm is preferably a maximum of 42, 41, 40, 39, 38, 37 or 36 at each instance. Any minimum and maximum can be combined to form a range. Suitable ranges include 29-40 μm, 30-38 μm, 30-36 μm, 29-36 μm or 29-34 μm.

In the examples, the surface roughness ($S_z$) was taken from the reading of a VHS-6000 digital microscope, rounded to the closest whole μm value.

Controlling the surface roughness impacts not only on the degree of uniformity of the film, but also on the stickiness of the film to the mould, and release of the cured film from the mould. The former must be rough enough for the liquid latex composition to stick, but then not so rough that there is over-sticking of the cured product. The applicant unexpectedly found a balance that allows for the commercial-scale production of ultra-thin gloves. The gloves could be produced on conventional glove-dipping lines (albeit with modifications to the formers, compositions and so forth), but without any slowing (or excessive slowing) of the production speed, which is critical to the overall cost of production of each unit of the product. Combining the surface roughness with low particle size for the mould release agent in the coagulant is also desirable.

In some embodiments, the surface roughness ($S_z$) of the palm zone of the former is different to that of one or both of the between finger zones and the finger zones.

In some embodiments, the palm and cuff zones together encompass at least 50% of the former surface (specifically, the dipping zone of the former surface), and the combined palm and cuff zone has a surface roughness within the ranges indicated previously for the palm zone.

In another embodiment, the former is a cuff-banded former. In this embodiment, the glove-shaped former comprises a cuff zone including a cuff band region with a roughened surface that is visible to the naked eye. The cuff band region suitably has a surface roughness ($S_z$) that is greater than that of the cuff zone outside the cuff band region. The cuff band region of the former provides resistance to slipping of a gelled latex composition on the former during a pre-leaching stage of glove production. The former is dipped in a fingers-down orientation, with the cuff band is at the uppermost end. The former is dipped into the latex until there is part-immersion of the cuff band region of the former into the latex, and then it is withdrawn, so that the upper edge of the latex on the former is within the cuff band region. Upon later gelling of the latex and washing stages, there can be slippage of the gelled latex down the former surface, creating defects. The cuff band region provides a zone of resistance at the upper end of the glove on the former that prevents the slippage of the gelled latex that may otherwise occur. Such a feature is of particular pertinence to the production of ultra-thin film gloves, where it has been found that there is a greater tendency for slippage. In some embodiments, the cuff band region has a surface roughness that is at least as high as, or higher than, the surface roughness of both the palm zone and the cuff zone. In some embodiments, the cuff band region surface roughness is a minimum of 110% of the palm zone surface roughness. In such a cuff-banded former, the surface roughness of the cuff-band region may be 30 μm or above, such as 33 μm or above. In the above discussion, the cuff zone refers to the part of the cuff zone outside the cuff band region.

The cuff band region may have an $S_z$ that is a minimum of 30, 31, 32, 33, 34, 35 or 36 μm. The $S_z$ is not specifically limited, but it could conceivably be as high as 36, 37, 38, 39, 40, 41, 42, 43, 44, 45, 46, 47, 48 μm or more. The minimum and maximums can be combined without limitation.

Figure 4:
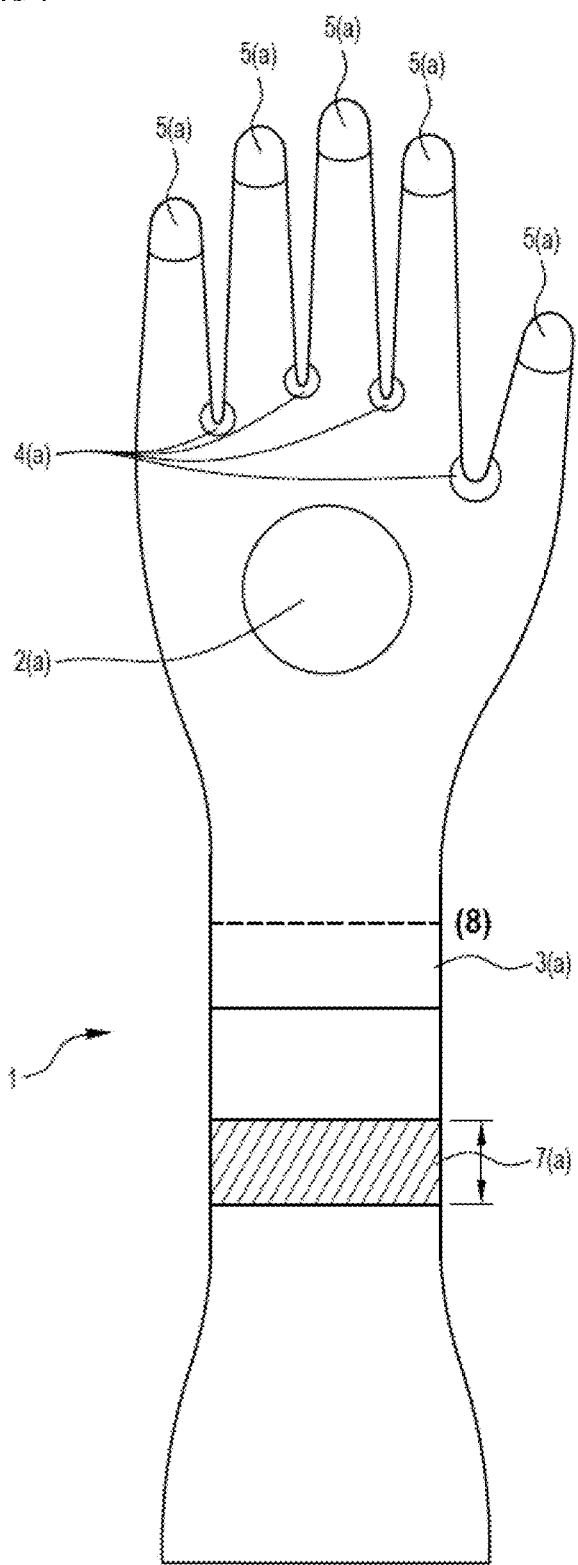
FIG. 4 is a schematic illustration of a former that may be used in the production of gloves in accordance with embodiments of the present invention.
Figure 5:
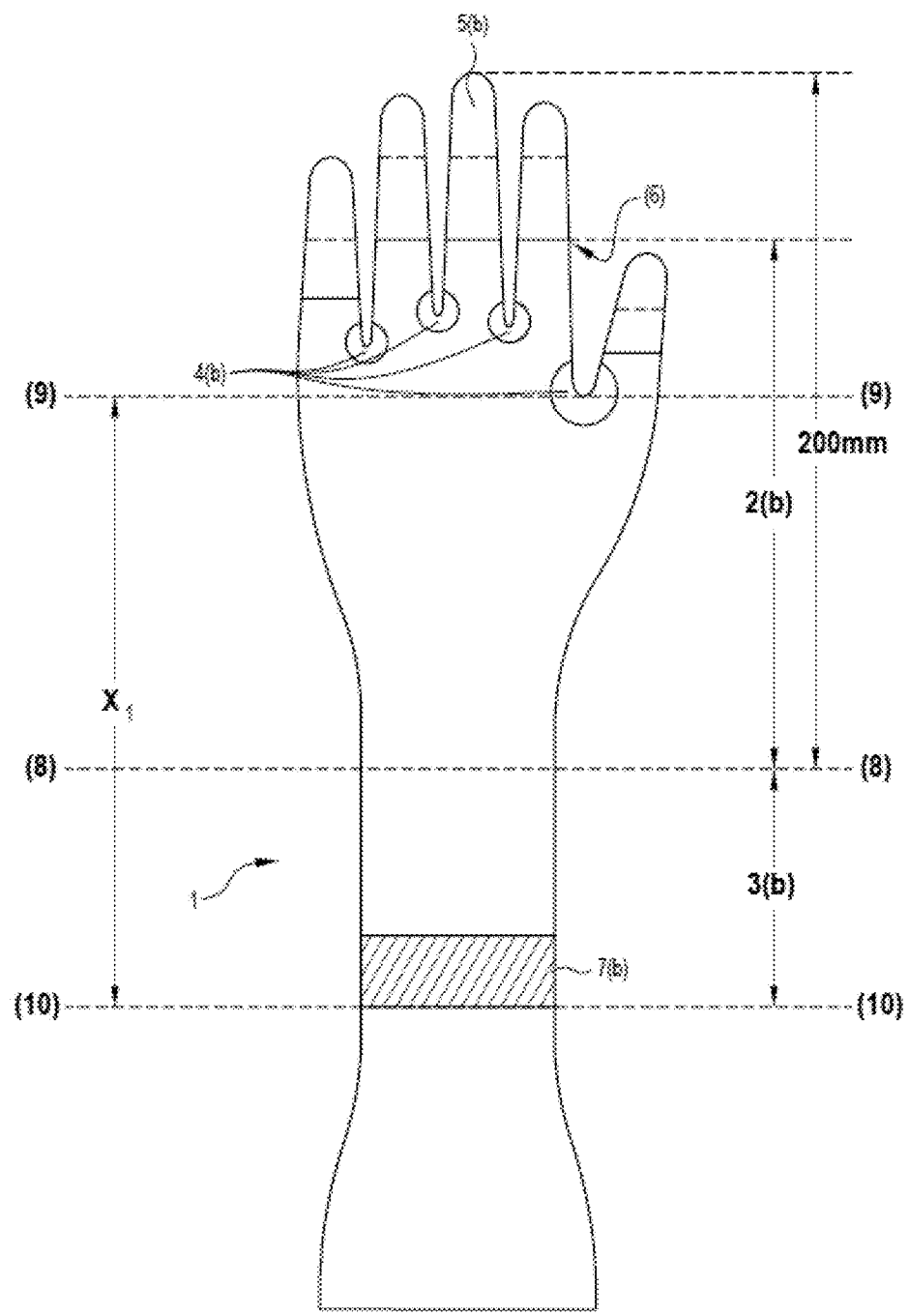
FIG. 5 is modified illustration of the former shown in FIG. 4 illustrating the maximum extent of the zones of the former.

The location of each of the zones (i)—the palm zone P, (ii) the cuff zone C, (iii) the between finger zone BF and (iv) the finger zone F are illustrated in FIGS. 4 and 5. This figure shows a glove former (1), with zones including a palm zone (2), a cuff zone (3), between finger zones (4) and finger (fingertip) zones (5). In FIG. 4, zones (2) to (5) are illustrated as being of a smaller size, denoted by an (a) after the number. In FIG. 5, the zones (2) to (5) are shown to be of a larger size, denoted by (b). Each of the zones may be defined as follows:

P: A palm zone ((2a) in FIGS. 4 and (2b) in FIG. 5) is in the region of the glove that corresponds to the palm of the hand. This may be present on each side of the former, and may be present as a continuous zone that extends around either side of the former, as each former is for the production of gloves of the same shape for wearing on both left or right hands. Thus, the palm zone typically extends around the middle part of the former between the fingers and the cuff. The palm zone is a minimum of 4 cm² (see (2(a)) in FIG. 4). The palm zone may extend as far as from the end finger zone (indicated by (6) in FIG. 5) to the start of the cuff zone (which generally commences around a line 200 mm from the most remote fingertip—marked by dashed line (8) in FIG. 5). A larger size version of the palm zone is indicated by (2(b)) in FIG. 5, although it is noted that the length of the palm zone will depend on where the cuff zone ends (see discussion below). When a plurality of palm zone surface roughness measurements are taken, these may, for example, be spaced evenly within the palm zone. For example, the measurements may be taken at the four corners of a 2 cm×2 cm square region in the centre of the palm zone.

C: The cuff zone extends as a band of at least 20 mm in width encompassing an area further than 200 mm from the most remote fingertip, as indicated by (3(a)) in FIG. 4. Typically the cuff zone encompasses a broader area of the former, covering the region between dashed line (8) as indicated in FIG. 5 (which is located 200 mm from the most remote fingertip) to dashed line (10), which corresponds to the anticipated dipping depth on the former. The cuff zone may extend further still, to encompass the area marked as X, in FIG. 5, extending from line (9) to line (10). The length of the cuff zone may therefore be anywhere between that indicated by (3(a)) in FIG. 4, to that indicated by $X_1$ in FIG. 5. According to embodiments described above, there may be a sub-section of the cuff zone, referred to as the cuff band region (marked as 7(a) in FIGS. 4 and 7(b) in FIG. 5), that has a higher roughness than the remaining cuff zone. The cuff band area may be a minimum of 20 mm in width (see (7(a)) in FIG. 4), and extends across a region of the former corresponding to the intended dipping depth. This may correspond to a beading zone of the glove. The cuff band area may be up to 40 mm in width (see (7(b) in FIG. 5).

BF: A between finger zone (4) refers to the crotch between adjacent finger portions of the former. The between finger zone is suitably a minimum area of 1 cm² of any suitable shape extending across the crotch area (see (4(a)) in FIG. 4). The between finger zone may extend to an area of up to about 4 cm² in size, of any suitable dimensions (see (4(b)) in FIG. 5).

F: The former includes 5 fingers (in this case, the thumb is classified as a finger). The finger zone (5) covers at least the first ⅓ of the finger length extending from the fingertip of each finger). The minimum size area is indicated by (5(a)) in FIG. 4. The finger zone may extend to ⅔ of the full length of the finger portion, starting at the fingertip (see (5(b)) in FIG. 5, terminating at the line indicated by numeral (6) in FIG. 5). The finger zone may extend further, such as to the end of the finger, where it may meet the start of the palm zone and the between finger zones. The finger zone excludes the between finger zone (4).

For any area between the zones that is not accounted for, the roughness may be set at any suitable value. Generally, the glove will be divided into zones such that each of the four zones indicated (plus the cuff band area of the cuff) will abut one another. As one example, the palm zone may extend part-way up the fingers of the former, ending at a point where the finger zone commences (e.g. point (6) in FIG. 5). There may be a gradual transition between the roughness of one zone and the next adjacent zone, or there may be a sharp delineation between adjacent zones.

It will be noted that the roughness values for some adjacent zones of the sets indicated above are the same, so there will be no need to distinguish between the end of one zone and the commencement of the next zone in such situations. Where the roughness values differ between adjacent zones, areas of different roughness will be detectable.

Control of Formation of Ultra-Thin Gloves

In some embodiments, the combination of the coagulant dipping step and the latex dip is controlled to ensure ultra-thin coatings onto the mould. A suitable combination of conditions according to particular embodiments are as follows:

Coagulant concentration of between 0-10%, based on multivalent ion concentration (e.g. calcium), such as between 0.1-10%, 1-10%, 0.1-7%, 1 and 7%, and preferably 1 and 5%;

Total time period covering lowering the mould into the coagulant tank, dwell time, and raising out of the coagulant tank of between 10 and 24 seconds;

A latex total solids content of about 1-20%, such as about 3 to about 12%;

A total time period covering lowering the mould into the latex dipping tank, dwell time, and raising out of the tank of between 15 and 24 seconds.

The conditions may comprise the mould release agent particle size as described previously. The conditions may comprise the content of mould release agent in the coagulant described previously. The conditions may comprise the formation of the glove on a former having the surface roughness properties as described above. The conditions may also comprise the concentration of cross-linking agent, as described previously. The conditions may also comprise the identity of the cross-linking agent(s), as described previously.

Finger Cots

The present application also extends to finger cots and methods for their manufacture.

Finger cots are disposable shields for the finger only, and are used in situations when a full glove is not necessary. Finger cots can be made by the same technique and using the same compositions as described above for glove production, with the one difference being the shape of the mould and the consequent shape/size of the product. A finger cot comprises a finger portion and a beaded rim. In the case of finger cots, the finger thickness is the indicator of the thickness of the overall product, and impacts on the weight of the product.

According to such aspects, there is provided a synthetic elastomeric finger cot with:

(a) a thickness of less than 0.05 mm;

(b) a modulus at 500% above 6.5 MPa; and/or (c) an elongation at break below 700%.

The thickness refers to the finger thickness. Preferred thicknesses for the finger thickness are as specified above in the context of the finger thickness for the gloves—although limited to a thickness of less than 0.05 mm.

The modulus and elongation values for the glove indicated above apply equally to the production of finger cots. Using the techniques described herein, it is possible to produce such ultra-thin finger cots having elongation and modulus values as described above.

According to the present invention there is also provided a method of manufacturing the synthetic elastomeric finger cot described above comprising:

dipping a finger-shaped former into an elastomeric film-forming composition;

curing the elastomeric film-forming composition on the former so as to produce the synthetic elastomeric finger cot.

The conditions for manufacture of the finger cot (including composition details) are as described above for the glove, with some modifications to be suited to finger cot production. One modification is that the former is a finger-shaped former. The finger-shaped former preferably has a surface roughness ($S_z$) that is between 28 and 42 μm, or between any of the narrower ranges indicated above for the palm zone of the controlled roughness former. The finger-shaped former also preferably has a band-region of higher surface roughness ($S_z$) than the surface roughness of a finger zone adjacent to the band-region. This corresponds to the cuff-band region in the glove-shaped former. Another modification is that the time period of dipping the mould into the coagulant, and into the latex (covering lowering, dwell, and raising), is shorter due to the smaller size/length of the mould which requires less time to lower and raise to become fully immersed in the coagulant or latex. The total time period is suitably half those specified for glove production indicated above.

In the claims and in the preceding description, except where the context requires otherwise due to express language or necessary implication, the word "comprise" or variations such as "comprises" or "comprising" is used in an inclusive sense, i.e. to specify the presence of the stated features but not to preclude the presence or addition of further features in various embodiments of the invention.

EXAMPLES

The invention will now be described in further detail with reference to the following non-limiting examples which involve the preparation of elastomeric film gloves.

General Procedure for Production of Elastomeric Gloves

In the examples set out below, the following general procedure was utilised to produce elastomeric gloves, unless indicated to the contrary.

1. Preparation of Cross-Linking Composition

One part sodium aluminate as the chosen multivalent metal source, together with 1 part sodium hydroxide and 1 part potassium hydroxide as alkali and 1 part glycerine as stabiliser, were combined with 6 parts of water. Then, one part of this initial concentrate was combined with 10 parts of water, to yield a cross-linking composition containing 96 parts water and 1 part of each of the sodium aluminate, NaOH, KOH and glycerine. The combination was heated at an elevated temperature (typically around 95° C., but anywhere from 80° C. to boiling point) to dissolve the multivalent metal, through the formation of negatively charged multivalent metal complex ions. The concentration of metal ions in the cross-linking compositions obtained was 0.66% or 0.33% by weight of total solution, respectively. The pH of the solution was in the range of about 12-13.

2. Preparation of Latex Composition

A commercially-available aqueous suspension of synthetic carboxylated polymer, supplied at a total solids content of about 45% or more, is diluted to an intermediate total solids content using 3% potassium hydroxide solution. The amount of potassium hydroxide solution added was such as to provide the amount of KOH indicated in the examples (phr). The actual total solids content to which the suspension is diluted is chosen based on the desired phr amount of KOH and the final total solids content of the dipping composition for the latex composition. The final total solids content may be anywhere between 3% and 15%. For a final latex composition having a total solids content of about 5 or 10%, as used in these examples, the initial dilution is to about 25%-30%. The pH of the diluted suspension so produced was above 9.0, typically in the range of 9.2 to 9.6.

The diluted suspension of synthetic carboxylated polymer is placed in a mixing vessel, and the surfactant is added. The amount and identity of the surfactant was as indicated in the examples. Next the cross-linking composition added very slowly with constant stirring. The cross-linking composition is added in an amount to provide the required phr of multivalent metal to the polymer. In view of the concentrations of the streams used in the examples, the relative amounts of the two components was about 0.1 parts of cross-linking composition to 100 parts polymer suspension. This further reduces the total solids content of the polymer closer to 20%.

Next, any second cross-linking agents were added. The sequence of addition was as follows. First, any solid zinc oxide or magnesium oxide was added (if used). Then, sulphur and sulphur donors were added.

Finally, a dispersion in water of final powder materials was added. This included the titanium dioxide and antioxidant. The amount of inclusion of each is as required to provide the target formulation for the latex composition. After addition of the solid components, the pH may be fine-tuned by the addition of further alkali (the 3% KOH solution in the present examples). The total solids content of the final formulation for the latex composition for the examples was about 5-10%. In other cases, it may be between 3% and 15% for the formation of thin film gloves.

3. Washing

The formers are subjected to pre-washing, to remove any remaining residues following removal of a glove previously made on the former. The formers are cleaned in mild acid/alkali and hot water. The formers are then dried by blowing air by blowers or air curtains or using ovens with the hot air having temperature above 105° C.

4. Coagulant Dipping

The cleaned dry former is immersed in a coagulant bath, which contains a 0-50% by weight solution of calcium nitrate. The coagulant also contains 0.1%-5.0% by weight metallic stearates, suitable wetting agents (0.001-1.0%) and antifoaming agents (0.001-1.0%). In some embodiments, coagulant dipping is not required. In the examples practiced here, the coagulant contained 2-4% calcium nitrate in addition to the above-indicated metallic stearates (calcium stearate), wetting agent and antifoaming agent. The total time period of dipping into the coagulant was about −10-24 secs, including the time period of lowering and raising into the coagulant (starting from the time when the mould first touches the surface of the coagulant composition, to complete removal from the coagulant composition.) This time period can apply to the embodiments described herein more generally, and should not be read as applying to these examples only.

5. Drying

The coagulant coated formers are dried in a hot air circulated oven at a temperature of about 110° C. to 130° C.

6. Dipping Step

The former, coated with dried coagulant, is dipped into a tank containing the latex composition described in step 2 above. The composition is maintained at temperature of around 20-35° C., and is constantly circulated in the tank to avoid creaming and settling of the solids. The former may be dipped into the composition for a total time period from the commencement of lowering into the latex (i.e. when the mould first touches the latex composition), to the end of raising of the mould (i.e. when the mould is completely removed from the latex) of between 2 and 60 seconds, and preferably from about 2 to about 15 seconds. In the examples practiced here, the lowering time period ("in") was about 2 to 6 seconds, the dwell time was about 0 to 8 seconds, and the raising time ("out") was about 3 to 15 seconds, with the total time period being about 5 to 30 seconds. These time periods can apply more generally across all embodiments described herein, and should not be read as applying to these examples only.

7. Drying

The composition coated formers are gelled in a gelling oven at a temperature of about 100-300° C. and the duration of 2-300 seconds. In the examples practiced here, the drying conditions were 110° C. for 60 seconds.

8. Pre-Leaching

This step is optional. In the case of single dipping of elastomer, preleaching is completed as per this sequence. In case of multiple dipping of latex composition, this step is completed after the final dip into the latex composition followed by gelling. Pre-leaching is conducted by rinsing in warm water for a short period of time. The gelled film coating on the former is pre-leached in series of tanks at a temperature anywhere between ambient and 95° C. In the examples it was typically about 55° C.

9. Second Dipping Step

This step is optional, and is performed if a further layer of elastomeric film is to be formed on the initial layer of elastomeric film-forming composition. The gelled elastomeric film coating on the former is dipped into a tank containing the latex composition, which contains the components specified for the given example (as prepared through step 2). The composition is maintained at temperature of around 20-40° C., and is constantly circulated in the tank to avoid creaming and settling of solids. The former is dipped into the composition for a dwell time of 5-90 seconds. In the examples practiced here, the second dip dwell time was 8 seconds.

10. Gelling/Pre Leaching/Beading

This preleaching step is optional, and is performed as per this sequence in the case of multiple dipping of latex composition after forming a further layer of elastomeric film. The product following the second dipping step is subjected to gelling and pre-leaching and beading. In the case of on-line polymer coating the sequence is gelling/preleaching/polymer coating/beading.

In the case of single dipping of elastomer, preleaching is completed as described above. The product following the dipping step is subjected to gelling and pre-leaching and beading. In the case of on-line polymer coating the sequence is gelling/preleaching/polymer coating/beading.

The beading, drying and pre-leaching steps can be carried out in any order. The processes of beading and pre-cure leaching could be exchange depending on the quality of cuff beading.

11. Curing

The beaded glove is then cured. Curing was conducted at about 80° C.-150° C. for about 15-30 minutes, depending upon the film thickness and intended end product physical properties.

12. Post-Leaching/Lubricant/Final Drying/Stripping/Tumbling

In the case of a glove product, the cured elastomeric article may be subjected to one or more process steps including post-leaching, chlorination (noting that this could alternatively take place before curing), neutralisation, additional curing/surface treatment and/or lubricant application (e.g. through dipping into a lubricant composition). The gloves will be stripped from the former and dried. Packaging may follow. Where additional curing or surface treatment is required, the gloves could be tumbled using hot air at a temperature around 80-120° C. for about 15-120 minutes.

Formers

Conventional formers as produced and supplied by a commercial supplier were used for Examples 1 to 5. The formers used in Examples 6 to 7 were as described in detail in those examples.

General Procedure for Production of Finger Cots

The same general procedure as described above for glove production can be used for the production of finger cots. The differences are the shape of the mould, and the dwell time in the coagulant and latex, which is halved (due to the shorter time period to reach complete immersion and complete removal from the coagulant/latex).

Test Procedure

For all of the Examples, tests were performed to determine the following properties of the films:

Modulus at 300%
Modulus at 500%
Tensile strength (MPa/Psi) (1 MPa=145 Psi);
Elongation (%); and
Load at Break (N %).

Tensile strength, stress at 300% and 500% modulus and elongation to break were measured by testing procedures conducted in accordance with ASTM D 412-06a (2013), based on the sample size set by the standard for gloves. The gloves were also tested for load at break (or force at break) measured in accordance with EN 455. The standards are readily available. These tests can be applied to multilayer films and gloves (such as examination gloves for medical applications). In all tables of results, the values indicated for the tensile strength, modulus at 300% and modulus at 500% are in units of MPa, and the elongation (or elongation at break) and the load at break in %.

Defects were measured and the results represented in terms of defects per million (DPM) or AQL. Statistical control was conducted as per ISO 2859-1 (refer to Tables I and IIA of ISO 2859-1), and quality control was performed as per ISO 13485.

General Formulation

Set out below is a typical formulation for the composition.

| Ingredients | Parts per Hundred Rubber (phr) - Dry basis (unless otherwise indicated) |
|---|---|
| Carboxylated synthetic polymer or blend | 100 |
| Alkali | 0.1-2.0 Sufficient to provide a pH of at least 9.0 |

-continued

| Ingredients | Parts per Hundred Rubber (phr) - Dry basis (unless otherwise indicated) |
|---|---|
| Cross-linking composition, comprising: | Added in an amount to provide the following: |
| negatively charged multivalent metal complex ions | 0.01-5.0, based on weight of metal ion per hundred parts rubber, by weight |
| alkali to solubilise and form the negatively charged multivalent metal complex ions in the cross-linking composition (providing a pH of at least 9.0 to the cross-linking composition) | 0.1-5.0 Sufficient to provide a pH of at least 9.0 |
| mechanical stabilizer for maintaining the metal complex ion in solution | 0-5.0 |
| Antiozonant | 0.0-5.0 |
| Covalent cross-linking agent | 0.0-4.0 |
| Insoluble ionic cross-linking agent | 0.0-4.0 |
| Sulphur and Sulphur donor cross-linking agents | 0.0-5.5 |
| Antioxidant | 0.2-3.0 |
| Opaqueness provider | 0.0-5.0 (when present, 0.01-5.0) |
| Pigment | As per requirement |
| Defoamer | 0-2.0, and if present 0.001-2.0 |

In each of the examples, a cross-linking composition was prepared from selected components of the overall formulation indicated, using step 1 of the general procedure outlined above. The cross-linking composition was combined with a commercially available synthetic polymer (the identity of which is outlined in the examples), in accordance with steps 2 and 3 of the general procedure, in amounts to produce the latex compositions set out in the relevant table. A glove was produced using the steps of the general procedure from the latex composition.

Example 1

Gloves were produced using the compositions shown below, each containing solubilised sodium aluminate.

| | | Composition in phr (parts per hundred parts of dry rubber) | | | | |
|---|---|---|---|---|---|---|
| Experiment no. | | A | B | C | D | E |
| Polymer | | 100 | 100 | 100 | 100 | 100 |
| KOH | | 1.5 | 1.5 | 1.5 | 1.5 | 1.5 |
| SDBS | | 0.2 | 0.2 | 0.2 | 0.2 | 0.2 |
| Cross linking composition: | Sodium aluminate | 0.1 | 0.15 | 0.2 | 0.25 | 0.3 |
| | NaOH | 0.1 | 0.15 | 0.2 | 0.25 | 0.3 |
| | KOH | 0.1 | 0.15 | 0.2 | 0.25 | 0.3 |
| | Glycerine | 0.1 | 0.15 | 0.2 | 0.25 | 0.3 |
| | Sulfur | 0.15 | 0.15 | 0.2 | 0.25 | 0.3 |

| | Composition in phr (parts per hundred parts of dry rubber) | | | | |
|---|---|---|---|---|---|
| Experiment no. | A | B | C | D | E |
| Zinc oxide | 0.2 | 0.3 | 0.4 | 0.5 | 0.6 |
| ZDBC | 0.05 | 0.05 | 0.1 | 0.15 | 0.2 |
| Antioxidant | 0.25 | 0.25 | 0.25 | 0.25 | 0.25 |
| $TiO_2$ | 2.5 | 2.5 | 2.5 | 2.5 | 2.5 |

Polymer = commercially available carboxylated acrylonitrile butadiene latex
Antioxidant is Lowinox CPL, a hindered phenolic antioxidant.
Sodium aluminate - the phr amounts refer to the total sodium aluminate. This was added in the form of a cross-linking composition containing solubilised sodium aluminate (in an amount of 0.1-0.3 phr based on the rubber), sodium hydroxide (0.1-0.3 phr), potassium hydroxide (0.1-0.3 phr), Glycerine (0.1-0.3 phr) and water, where the water concentration in the cross-linking composition was 96%.

The gloves were produced in accordance with the general procedure outlined above, using the dipping parameters for different sized gloves as set out in the table below:

| | Dipping parameters | | |
|---|---|---|---|
| Glove size | 2 gram | 1 gram | 0.5 gram |
| Calcium Nitrate (%) | 4 | 4 | 2 |
| Latex TSC (%) | 10 | 10 | 5 |
| Dwell Time | In (4 sec)-Dwell (8 sec)-Out (13 sec) | In (3 sec)-Out (6 sec) | In (3 sec)-Out (6 sec) |
| Layer | Double Dip | Single Dip | Single Dip |

Dimensions of the gloves are set out in the table below:

| | | Dimensions | | | |
|---|---|---|---|---|---|
| Glove size | Experiment no. | Weight (g) | Cuff (mm) | Palm (mm) | Finger (mm) | Average thickness (mm) |
| 2 gram | A | 2.009 | 0.038 | 0.045 | 0.059 | 0.047 |
| | B | 2.018 | 0.034 | 0.038 | 0.057 | 0.043 |
| | C | 2.024 | 0.036 | 0.038 | 0.059 | 0.045 |
| | D | 1.971 | 0.034 | 0.042 | 0.057 | 0.044 |
| | E | 1.906 | 0.037 | 0.044 | 0.057 | 0.046 |
| 1 gram | A | 1.196 | 0.020 | 0.026 | 0.038 | 0.028 |
| | B | 1.231 | 0.023 | 0.028 | 0.039 | 0.030 |
| | C | 1.162 | 0.021 | 0.024 | 0.034 | 0.026 |
| | D | 1.205 | 0.022 | 0.028 | 0.039 | 0.029 |
| | E | 1.173 | 0.023 | 0.029 | 0.039 | 0.031 |
| 0.5 gram | A | 0.725 | 0.017 | 0.024 | 0.038 | 0.026 |
| | B | 0.775 | 0.016 | 0.027 | 0.034 | 0.026 |
| | C | 0.510 | 0.006 | 0.008 | 0.021 | 0.012 |
| | D | 0.526 | 0.009 | 0.018 | 0.020 | 0.015 |
| | E | 0.506 | 0.015 | 0.017 | 0.025 | 0.019 |

The properties of the films produced were tested and are set out in the tables below: 2 gram glove

| | Unaged | | | | | Aged (100° C. 22 hours) | | | | |
|---|---|---|---|---|---|---|---|---|---|---|
| Expt no. | Tensile (Mpa) | EB (%) | M300 (Mpa) | M500 (Mpa) | LB (N) | Tensile (Mpa) | Elongation (%) | Mod@300 (Mpa) | Mod@500 (Mpa) | LB (N) |
| A | 32.32 | 580 | 5.45 | 17.21 | 2.94 | 36.29 | 620 | 5.01 | 15.92 | 3.84 |
| B | 31.95 | 640 | 2.77 | 7.03 | 2.9 | 33.76 | 630 | 3.34 | 9.51 | 3.07 |
| C | 29.55 | 620 | 4.19 | 12.34 | 2.69 | 39.83 | 600 | 4.6 | 15.54 | 3.62 |
| D | 33.3 | 600 | 4.95 | 14.98 | 3.03 | 39.74 | 600 | 6.52 | 20.86 | 3.61 |
| E | 33.63 | 560 | 7.1 | 27.02 | 3.06 | 35.02 | 540 | 7.19 | 25.06 | 3.18 |

Analysis of Results:

The produced low weight gloves have good physical properties.

For the 2 gram glove, the before aging tensile strength values were between 30 MPa and 34 MPa, and the after aging tensile strength values were between 35 MPa and 40 MPa. Considering the ASTM Standard Specification for Nitrile rubber examination gloves (ASTM D6319) minimum requirement of 14 MPa for examination gloves, these glove will pass the strength criteria comfortably even though they are low weight. Specifically, the gloves of the present application do not meet the minimum thickness required in ASTM D6319, but regardless, these meet the tensile strength requirements. This is a significant achievement given the ultra-low thickness (below ASTM mandated levels for nitrile gloves).

The before aging elongation at break is between 640% and 560% at unaged condition and between 630% and 540% in the accelerated aging condition at 100° C., for 22 hrs. Against the ASTM Standard Specification for Nitrile rubber examination gloves (ASTM D6319) minimum requirement of 500% unaged and 400% after accelerated aging, the 2 gram gloves of Example 1 surpass the requirements. Again, the gloves of the present application do not meet the minimum thickness required in ASTM D6319, but regardless, these meet the elongation at break requirements. This is a significant achievement given the ultra-low thickness (below ASTM mandated levels for nitrile gloves).

The gloves produced showed no visible signs of defects or holes. The glove film surface was complete and cohesive across the entire glove.

The above results may imply that low weight gloves with good properties may be produced. Because the gloves are low weight, less material is required to make these gloves, which allows them to be produced at lower cost.

Example 2

Gloves were produced using the compositions shown below.

| | Composition in phr (parts per hundred parts of dry rubber) Experiment no. | | | |
|---|---|---|---|---|
| | G | H | I | J |
| Polymer | 100 | 100 | 100 | 100 |
| KOH | 1.5 | 1.5 | 1.5 | 1.5 |
| Sulfur | 0.15 | 0.2 | 0.25 | 0.3 |
| Zinc oxide | 1.0 | 1.25 | 1.5 | 1.75 |
| ZDBC | 0.05 | 0.1 | 0.15 | 0.2 |
| Antioxidant | 0.25 | 0.25 | 0.25 | 0.25 |
| TiO$_2$ | 2.5 | 2.5 | 2.5 | 2.5 |

Polymer = commercially available carboxylated acrylonitrile butadiene latex.
Antioxidant is Lowinox CPL, a hindered phenolic antioxidant.

The gloves were produced in accordance with the general procedure outlined above, using the dipping parameters for different sized gloves as set out in the table below:

| | Dipping parameters Glove weight | | |
|---|---|---|---|
| | 2 gram | 1 gram | 0.5 gram |
| Calcium Nitrate (%) | 4 | 4 | 2 |
| Latex TSC (%) | 10 | 10 | 5 |
| Dwell Time | In (4 sec)-Dwell (8 sec)-Out (13 sec) | In (3 sec)-Out (6 sec) | In (3 sec)-Out (6 sec) |
| Layer | Double Dip | Single Dip | Single Dip |

Dimensions of the gloves are set out in the table below:

| Glove weight | Experiment no. | Weight (g) | Cuff (mm) | Palm (mm) | Finger (mm) | Average thickness (mm) |
|---|---|---|---|---|---|---|
| 2 gram | G | 1.779 | 0.029 | 0.037 | 0.051 | 0.039 |
| | H | 1.775 | 0.031 | 0.037 | 0.055 | 0.041 |
| | I | 1.808 | 0.035 | 0.043 | 0.059 | 0.046 |
| | J | 1.801 | 0.033 | 0.041 | 0.062 | 0.045 |
| 1 gram | G | 1.074 | 0.019 | 0.025 | 0.031 | 0.025 |
| | H | 1.062 | 0.020 | 0.027 | 0.036 | 0.028 |
| | I | 1.074 | 0.018 | 0.025 | 0.039 | 0.027 |
| | J | 1.089 | 0.085 | 0.029 | 0.038 | 0.051 |
| 0.5 gram | G | 0.500 | 0.007 | 0.010 | 0.013 | 0.010 |
| | H | 0.503 | 0.008 | 0.011 | 0.015 | 0.011 |
| | I | 0.505 | 0.007 | 0.011 | 0.016 | 0.011 |
| | J | 0.503 | 0.008 | 0.012 | 0.016 | 0.012 |

The properties of the films produced were tested and are set out in the tables below:

| | 2 gram glove | | | | | | | | | |
|---|---|---|---|---|---|---|---|---|---|---|
| | Unaged | | | | | Aged (100° C. 22 hours) | | | | |
| Expt no. | Tensile (Mpa) | EB (%) | M300 (Mpa) | M500 (Mpa) | LB (N) | Tensile (Mpa) | Elongation (%) | Mod@300 (Mpa) | Mod@500 (Mpa) | LB (N) |
| G | 24.38 | 610 | 2.99 | 7.97 | 2.22 | 29.08 | 630 | 3.43 | 10.31 | 2.64 |
| H | 29.21 | 620 | 4.07 | 12.08 | 2.65 | 33.58 | 600 | 4.9 | 20.23 | 3.05 |
| I | 39.03 | 600 | 9.01 | 27.55 | 2.37 | 43.12 | 620 | 6.03 | 22.2 | 3.92 |
| J | 26.13 | 580 | 6.44 | 18.93 | 2.38 | 40.28 | 620 | 6.32 | 19.56 | 3.66 |

Analysis of Results:

The produced low weight gloves have good physical properties.

For the 2 gram glove, the unaged tensile strength values were between 24 MPa and 40 MPa, and the after aging tensile strength values were between 33 MPa and 44 MPa. Considering the ASTM Standard Specification for Nitrile rubber examination gloves (ASTM D6319) minimum requirement of 14 MPa for examination gloves, these glove will pass the strength criteria even though they are low weight.

The M300 value varies from 2 to 10 MPa and M500 values varies from 7 to 28 Mpa in the before aging condition. M300 value varies from 3 to 7 and M500 value varies from 10 to 23 in the aged condition. This indicates that the film is strong enough to withstand the intended use.

The elongation at break is between 580% and 620% in the unaged condition, and the elongation at break is between 600% and 630% in the accelerated aging condition at 100° C., for 22 hrs. Against the ASTM Standard Specification for Nitrile rubber examination gloves (ASTM D6319) minimum requirement of 500% unaged and 400% after accelerated aging, the 2 gram gloves of Example 2 surpass the requirements.

The gloves produced showed no visible signs of defects or holes. The glove film surface was complete and cohesive across the entire glove.

The above results may imply that low weight gloves with good properties may be produced. Because the gloves are low weight, less material is required to make these gloves, which allows them to be produced at lower cost.

Example 3

Finger cots are produced using compositions A-E and G-J as indicated above, using the same coagulant and dipping parameters as indicated for the formation of gloves, with the exception that the mould is a finger-shaped mould, and the duration of the dipping step is:
In—1-2 seconds; Dwell—0-3 seconds; Out—1-5 seconds.

Example 4

Gloves of a nominal 2.2 grams in weight (noting that the actual weight may be between 2.0 and 2.2 grams) were produced using the compositions shown below. These compositions are based on a major proportion of nitrile butadiene rubber, and a minor portion of either polyisoprene or polychloroprene.

| Experiment no. | | A | B | C | D | E | F |
|---|---|---|---|---|---|---|---|
| XNBR | | 95 | 90 | 85 | 95 | 90 | 85 |
| Polyisoprene | | 5 | 10 | 15 | 0 | 0 | 0 |
| Polychloroprene | | 0 | 0 | 0 | 5 | 10 | 15 |
| KOH | | 1.5 | 1.5 | 1.5 | 1.5 | 1.5 | 1.5 |
| SDBS | | 0.3 | 0.3 | 0.3 | 0.3 | 0.3 | 0.3 |
| Cross linking composition: | Sodium aluminate | 0.25 | 0.3 | 0.35 | 0.25 | 0.3 | 0.35 |
| | NaOH | 0.25 | 0.3 | 0.35 | 0.25 | 0.3 | 0.35 |
| | KOH | 0.25 | 0.3 | 0.35 | 0.25 | 0.3 | 0.35 |
| | Glycerine | 0.25 | 0.3 | 0.35 | 0.25 | 0.3 | 0.35 |
| Sulfur | | 0.15 | 0.25 | 0.35 | 0.15 | 0.25 | 0.35 |
| Zinc oxide | | 0.5 | 0.75 | 1.0 | 0.5 | 0.75 | 1.0 |
| ZDBC | | 0.05 | 0.1 | 0.2 | 0.05 | 0.1 | 0.2 |
| Antioxidant | | 0.25 | 0.25 | 0.25 | 0.25 | 0.25 | 0.25 |
| $TiO_2$ | | 2.5 | 2.5 | 2.5 | 2.5 | 2.5 | 2.5 |

XNBR was a commercially available carboxylated nitrile butadiene rubber.
Antioxidant as above.

A conventional former was used for the preparation of the 2.2 gram gloves of this example.

The gloves were made via a single dip of the former into the coagulant composition described below (in 6 seconds, dwell 4 seconds, out 6 seconds), and a single dip into the elastomeric film-forming composition set out above (in 5 seconds, dwell 6 seconds, out 7 seconds.)

The coagulant had the following properties:
8.5-10.5% calcium nitrate (which is dissolved),
2.0-3.0% calcium stearate, with a particle size of 8-15 microns (as mould release agent)
0.1% of octyl phenol ethoxylate surfactant.
Balance water.

The gloves produced by this method were found to have a thickness at the palm of less than 0.050 mm, i.e. 0.04 mm, passed the freedom from holes test of ASTM D5151, and had the following properties:

| Physical properties (unaged) | | | | | | |
|---|---|---|---|---|---|---|
| Tensile (MPa) | 21.01 | 18.55 | 16.14 | 23.44 | 19.05 | 17.72 |
| M500 (MPa) | 9.52 | 11.2 | 11.46 | 10.51 | 12.91 | 12.54 |
| EB (%) | 600 | 540 | 540 | 593 | 540 | 540 |
| Force at Break (N) | 2.48 | 2.45 | 2.16 | 2.93 | 2.4 | 2.52 |
| Physical properties (aged) | | | | | | |
| Tensile (MPa) | 30.77 | 28.7 | 21.13 | 33.91 | 33.34 | 26.45 |
| M500 (MPa) | 17.39 | 21.71 | 18.56 | 21.81 | 22.24 | 14.68 |
| EB (%) | 600 | 560 | 540 | 600 | 580 | 600 |
| Force at Break (N) | 3.26 | 2.87 | 2.56 | 3.72 | 3.44 | 2.77 |

Example 5

Production scale (commercial scale) batches of gloves having weights of (a) 2.2 grams and a palm thickness below 0.05 mm (including an average thickness less than 0.05 mm) were produced on a standard glove production line with a standard former, albeit with controlled formulations and dipping times. The compositions used for each of the gloves were as follows:

| Formulation | 2.2 gram gloves (phr amounts) |
|---|---|
| Nitrile latex | 100 |
| KOH | 1.5 |
| SDBS | 0.2 |
| Colloidal Sulfur | 0.2 |
| ZDBC | 0.15 |
| ZnO | 0.45 |
| Anti-oxidant | 0.1 |

-continued

|  | 2.2 gram gloves (phr amounts) |
| --- | --- |
| Cross-linking solution: | |
| Sodium Aluminate | 0.3 |
| KOH | 0.6 |
| Glycerine | 0.3 |

The nitrile latex was a commercially available carboxylated nitrile butadiene rubber

|  | % by weight |
| --- | --- |
| Coagulant | |
| Calcium Nitrate % by weight | 8.5-10.5 |
| Calcium Stearate % by weight (CaSt) | 2.0-3.0 |
| Particle size of CaSt (micron) | 8-15 |
| octyl phenol ethoxylate surfactant | 0.1 |
| Coagulant Dipping Profile | |
| In (seconds) | 6 |
| Dwell (seconds) | 4 |
| Out (seconds) | 6 |
| Latex Dipping Conditions | |
| Latex TSC-Tank I | 12.5-13.5 |
| pH-Tank II | 9.2-10.2 |
| Latex Dipping Profile - Tank I | |
| In (seconds) | 6 |
| Dwell (seconds) | 6 |
| Out (seconds) | 7 |
| Latex TSC-Tank II | NA |
| pH-Tank II | NA |
| Latex Dipping Profile - Tank II | |
| In (seconds) | 5 |
| Dwell (seconds) | 6 |
| Out (seconds) | 7 |

32 samples of the 2.2 gram gloves were tested for tensile strength, modulus at 500%, and elongation. Before aging and after aging results were produced for each sample, where after aging was based on an accelerating aging test at 100° C. for 22 hours. As the production run progressed, the variation between samples reduced, and the glove properties became more uniform. The average results for the tested samples were as follows:

| Weight | Tensile strength (MPa - before aging) | Tensile strength (MPa - after aging) | Modulus at 500 (MPa - before aging) | Modulus at 500 (MPa - after aging) | Elongation (% - before aging) | Elongation (% - after aging) |
| --- | --- | --- | --- | --- | --- | --- |
| 2.2 grams | 27.8 | 32.7 | 14.75 | 14.7 | 585 | 585 |

In the production run, at the start, the glove tearing at the stripping station was high (17%, 10%, 5%) and the number of un-stripped gloves going for second dipping (without the complete removal from first dip) was high, to the tune of 3%. With due corrective action with respect to the adjusting the percentage amount of anti-tack (mould release agent) in the coagulant and proper cleaning, the strip reject (i.e. the percentage of gloves that were not successfully stripped from the former) came down below 2%, and then below 1%. The number of un-stripped gloves going for second round of dipping was reduced from 3% to 0.01%, and then down further to 0%.

The auto stripping machine clamps were re-adjusted to avoid tearing during stripping. The cleaning brushes at former cleaning stage were adjusted to minimise the powder mark in the gloves.

A fine balance needs to be struck between the avoidance of a powder mark (from the particulate mould release agent) and easy stripping of the gloves.

There was some inconsistency noticed in the barrier defect (pin hole defects) rate. The pin hole level in the early stages of the trial was higher, at about AQL 4.0 (as determined by ISO 2859-1), and then this slowly come down to less than AQL 2.5 and even less than AQL 1.0 or at times less than AQL 0.65.

Through the production scale trials, while it was possible to produce thin gloves with the required physical properties and without defects, some challenges were faced. These included a lower-than-desired effectiveness rate for machine-stripping, and higher-than desired defect rates such as pin-hole defects and tearing.

Example 6

Former Modification

The idea was developed to modify the former surface roughness in an attempt to improve the physical properties of the ultra-thin film gloves, and in particular the properties of batches (e.g. 500 glove batches) of ultra-thin film gloves.

Glass formers having a highly uniform surface were considered, but these produce shiny films and require different systems for allowing the right amount of elastomeric film-forming composition to be picked up onto the former. Further, glass formers require lower speed dipping lines, which impacts on the viability of the product from a production cost perspective.

Smooth glove-shaped formers denoted "1", "2" and "3" were sourced, based on ceramic formers with a glazed surface Gloves were made on these formers using the latex formulation of Example 1B set out above, with the latex TSC being 13% and the pH 10.07. The coagulant had a calcium nitrate concentration of 9.38% by weight, and calcium stearate of 2.42% (based on a particle size of between 3-13 micron—that is, 95% of the particles were between 3 and 13 micron). Gloves of 1.8 grams in weight were produced, and these were subjected to the conventional testing protocols using Die D. The results are set out in the table below.

| Former No | Weight (grams) | Test results | Unaged | Aged |
| --- | --- | --- | --- | --- |
| 1 | 1.8 | Thickness (mm) | 0.03 | 0.04 |
|  |  | Tensile (Mpa) | 33.15 | 33.61 |
|  |  | M500 (Mpa) | 13.86 | 22.15 |
|  |  | EB (%) | 620 | 600 |
|  |  | FAB (N) | 2.99 | 4.05 |
| 2 |  | Thickness (mm) | 0.03 | 0.04 |
|  |  | Tensile (Mpa) | 38.25 | 33.34 |
|  |  | M500 (Mpa) | 19.48 | 22.43 |

-continued

| Former No | Weight (grams) | Test results | Unaged | Aged |
|---|---|---|---|---|
| 3 | | EB (%) | 580 | 560 |
| | | FAB (N) | 3.45 | 4.01 |
| | | Thickness (mm) | 0.04 | 0.04 |
| | | Tensile (Mpa) | 22.13 | 32.69 |
| | | M500 (Mpa) | 13.71 | 18.83 |
| | | EB (%) | 580 | 580 |
| | | FAB (N) | 2.66 | 3.93 |

Example 7

Former Roughness Testing and Control

Further work was conducted to test the properties of ultra-thin film gloves produced using a more extensive range of formers.

A ceramic former supplier was directed to produce formers with varying roughness levels. These formers were denoted formers V4-V12. The formers were made from a ceramic material, and dried/cured to a so-called green-state or "biscuit state". The formers were then subjected to either sand blasting followed by high temperature firing (kiln firing), or sand (or ceramic compound) spraying followed by high temperature firing (kiln firing). Some formers were produced with ceramics containing agents for producing a more glassy surface during the firing step, to increase the smoothness of the surface. Between 3 and 5 of each former type were supplied for testing.

Objective

Tests were conducted to evaluate the performance of the formers made with different degrees of sand blasting as a means to adjust the former roughness. Gloves produced on the formers were tested for the quality of film (barrier, powder mark, slippage of film resulting in beading imperfection), difficulty to remove from the former and glossy nature of the glove end product.

Assumptions and System Followed

The trial formers V4 to V12 (between 2 and 5 of each) were fixed in a standard glove production line and were subjected to a minimum 2 week testing period using a consistent coagulant and latex formulations to produce production-scale quantities of gloves using each former. A control former (conventional former design) was also used to produce comparative gloves based on the same formulations and processing conditions.

The glove products were collected former-wise, and type wise, and the results were analysed in these categories. The glove products were inspected in line with established quality system management in accordance with the relevant standards. Statistical control was conducted as per ISO 2859, and quality control was performed as per ISO 13485.

Results a. Barrier Function

The barrier function test (pin hole detection test) was performed to assess the properties of the films produced on formers V4 to V12. Large numbers glove samples were produced from each former (noting that there were between 3-5 formers of each type) and analysed for holes at the palm (HOLE P or HP), at the cuff (HOLE CF or HCF), at the finger crotch (HOLE CR or HCR), and at the fingertip area (HOLE F or HF). The sample size for each former was: V4-360 gloves; V5-540 gloves; V6-900 gloves; V7-540 gloves; V8-900 gloves; V9-480 gloves; V10-900 gloves; V11-900 gloves; V12-900 gloves. The results are presented below.

| Former Type | TOTAL HOLE |
|---|---|
| V4-1 | 4 |
| V4-2 | 4 |
| V5-1 | 14 |
| V5-2 | 14 |
| V5-3 | 14 |
| V6-1 | 12 |
| V6-2 | 12 |
| V6-3 | 12 |
| V6-4 | 12 |
| V6-5 | 12 |
| V7-1 | 12 |
| V7-2 | 12 |
| V7-3 | 12 |
| V8-1 | 11 |
| V8-2 | 11 |
| V8-3 | 11 |
| V8-4 | 11 |
| V8-5 | 11 |
| V9-1 | 15 |
| V9-2 | 15 |
| V9-3 | 15 |
| V9-4 | 15 |
| V10-1 | 5 |
| V10-2 | 5 |
| V10-3 | 5 |
| V10-4 | 5 |
| V10-5 | 5 |
| V11-1 | 14 |
| V11-2 | 14 |
| V11-3 | 14 |
| V11-4 | 14 |
| V11-5 | 14 |
| V12-1 | 5 |
| V12-2 | 5 |
| V12-3 | 5 |
| V12-4 | 5 |
| V12-5 | 5 |

For the V8, V10 and V12 formers, the total barrier defects are 11, 5, 5 respectively—i.e. for V8 there are 11/900 pieces (12,222 DPM), V10-5/900 pcs (5556 DPM) and V12-5/900 pcs (5556 DPM). In total, there are 21/2700 pcs (7777 DPM), where DPM means defects per million pieces.

However, comparing these results to tear defects (results shown below), it will be noted that the tear defects obtained were extremely high for these three formers—V8-67/900 (74,0444 DPM); V10-85/900 (94,444 DPM); V12-136/900 (151,111 DPM).

The tear defects were caused by the stripping machine due to the slipping and/or the inability for the auto-stripping machine to grip the gloves. Another issue is the high surface gloss of gloves produced from some of the former types.

b. Hole-Finger, Palm and Total

Out of 6420 pieces checked in total there were 12 pinhole defects at Finger (HF)—12/6420-0.19% (1869 DPM). In the case of the Control (regular former) the HF defects found to be 99/6420-1.54% (15420 DPM).

The total (pin-hole) defects were as indicated below:

| Type | Total barrier defects per million (DPM) | % |
|---|---|---|
| V4 | 11111 | 1.11 |
| V5 | 25926 | 2.59 |
| V6 | 13333 | 1.33 |

-continued

| Type | Total barrier defects per million (DPM) | % |
|---|---|---|
| V7 | 42593 | 4.26 |
| V8 | 12222 | 1.22 |
| V9 | 39583 | 3.96 |
| V10 | 5556 | 0.56 |
| V11 | 15556 | 1.56 |
| V12 | 5556 | 0.56 |
| Control | 50467 | 5.05 |

The control formers had the defect level of 50467 DPM (324/6420) (run at the same time and under the same conditions). Compared to the regular (control) formers the defect level of the V4-V12 formers is less.

The number of palm defects (pin-hole defects at the palm) for each former type V4-V12 and Control is set out in the table below.

| Former Type | Hole Palm | % |
|---|---|---|
| V4 | 2700 | 0.27 |
| V5 | 13000 | 1.3 |
| V6 | 5000 | 0.50 |
| V7 | 24000 | 2.4 |
| V6 | 1000 | 0.1 |
| V9 | 8000 | 0.8 |
| V10 | 1000 | 0.1 |
| V11 | 3000 | 0.3 |
| V12 | 0 | 0 |
| Control | 12000 | 1.2 | c. Powder Mark

In relation to the visual appearance of the glove, a key defect that can be detected (particularly in coloured products) is a powder mark, in which residual powder adheres to the glove by accumulation on the former and later transfer onto the glove to leave a white patch or mark. In dark coloured products powder marks can be very obvious, and this leads to rejection of the gloves by customers.

The presence or absence of a powder mark was studied in the gloves produced on all the trial formers and compared to the control former following conventional inspection and recording procedures. The results of the powder mark testing were as follows:

| Type | Powder Mark (DPM) | Total inspected |
|---|---|---|
| V4 | 11111 | 360 |
| V5 | 1851 | 540 |
| V6 | 12222 | 900 |
| V7 | 5556 | 540 |
| V8 | 6667 | 900 |
| V9 | 6250 | 480 |
| V10 | 0 | 900 |
| V11 | 1111 | 900 |
| V12 | 0 | 900 |
| Trial | 4517 (actual defective gloves in V4-V12 trial) | 6420 |
| Control | 17290 (actual defective gloves) | 6420 |

There are two types are former with a much more shiny polished surface than the other formers. In these two cases, there were no powder marks detected across the 1800 checked pieces.

The inventors have postulated that the anti-tack material used in the coagulant gets accumulated in the micro-sized crevices of the former surface and anti-tack powder material is then transferred to the glove once the accumulation is substantial. Controlling the roughness of the former may enable a manufacturer to reduce the accumulation of anti-tack material and hence powder marks may be avoided.

The table includes in the second last line the overall average for all the trial formers put together. The defect level as a % of tested gloves was 0.45%, compared to the control former results of 1.73% powder mark defects.

d. Glossiness or Shining of Gloves

The glove samples produced on each former were assessed for surface gloss, and the number of gloves considered defective for excess glossiness was determined for each former type. The results are set out below:

| Former | V4 | V5 | V6 | V7 | V8 | V9 | V10 | V11 | V12 |
|---|---|---|---|---|---|---|---|---|---|
| Shining rate | 0 | 0 | 2 | 1 | 3 | 1 | 4 | 2 | 5 |

Formers V6, V8, V10 and V12 were more glossy than formers V4, V5, V7, V9 and V11.

Grouping these together and comparing the results by reference to defects per million (DPM), the following results are obtained:

| Former type | Total number of shiny gloves | DPM |
|---|---|---|
| V4, V5, V7, V9, V11 | 4 | 1418 |
| V6, V8, V10, V12 | 14 | 3889 |

The results show that the degree of gloss of former surface has an impact on the gloss level of the glove product, amongst other things. Whilst this may be a detraction for some products, a benefit with a glossy surface is that residues do not stick easily to the former surface, making the former easier to clean.

In glove production, a glossy glove surface is undesirable. Glossy gloves give the consumer the impression that the glove is slippery, and will result in slipping of items held by a gloved hand, particularly in applications where there is water contact (e.g. washing).

Even where a film produces a good quality barrier (in terms of pin-hole defects, and high tensile strength), the visual appearance and slipperiness associated with a low roughness former detracts from the selection of a former with extremely low surface roughness for producing gloves (either thin film or otherwise).

e. Film Strength

Tests were performed on the tensile strength of the films/gloves produced using the former types. M500 and elongation at break (%) were also measured. The results were as follows:

| Former | V4 | V5 | V6 | V7 | V8 | V9 | V10 | V11 | V12 |
|---|---|---|---|---|---|---|---|---|---|
| Tensile strength (MPa) | 34.49 | 25.75 | 30.88 | 26.57 | 39.32 | 37.35 | 29.34 | 25.89 | 48.31 |
| M500 (Mpa) | 15.6 | 10.2 | 13.0 | 18.0 | 20.5 | 21.2 | 15.5 | 12.7 | 24.6 |
| Elongation (%) | 607.0 | 614.0 | 600.0 | 567.0 | 587.0 | 573.0 | 574.0 | 594.0 | 594.0 |

While the highest tensile strength was obtained for the V12 type former, as noted above, this former produced gloves that are excessively glossy and with higher slip properties. It was observed that high surface roughness results in low tensile strength and low surface roughness results in high tensile strength. To obtain optimum quality characteristics such as high tensile strength, low visual defects, no shininess, fewer barrier defects and less slipperiness, a combination of former roughness characteristics at various points was selected, to produce a new former V13 as outlined in further detail below.

f. Coagulant Coating

The inventors observed during the test work that there was improved coagulant coating on the surface of the test formers compared to conventional formers, and the coagulant was able to stay within the crevices of the mould and remain as a coating on the entire dipped portion of the mould surface. This is important for even pickup and even coating of the elastomeric film-forming composition.

g. Powder Residue on the Former

The inventors observed during the test work that there was a greater tendency for powdery residue to build up on formers V4 and V6.

h. Slip Down at the Wet Gel Stage

The inventors also observed during the test work that a more glossy former surface could lead to a greater tendency for the elastomeric film-forming composition to "slip down" the former surface from the top of the cuff area towards the body of the glove during the wet gel stage. The inventors then developed a cuff band area at a one end (the upper end in the former-dipping orientation) within the cuff zone having a visually-observable roughened or scored surface. The cuff band area is more textured (rougher or more scored) than the remainder of the cuff portion of the former. Providing this band gave an improvement in the gripping of the wet gel to the mould and avoided slippage of the gel-state film down the former. During later stages of the production of the glove, the cuff band area is beaded or rolled to form a beaded opening to the glove.

i. Slip Down after Pre-Leaching

Pre-leaching during glove production is intended to remove soluble material in the wet gel and reduce the presence of contaminants. Improper removal of such contaminants will affect the performance of the gloves on usage or during storage. When the wet gel coated formers travel through the pre-leaching station, they are subjected to direct fluid forces acting on the former and gel by the movement of the formers inside the pre-leach water bath. If the adhesion of the gel to the former is not good enough, the film will be distorted.

The inventors found that there was a greater tendency for slipping to during this stage for formers of higher glossiness—V10 and V12. In the worst case, such slippage is observed by the presence of a fold or pleat in the glove surface. Accordingly, the surface roughness is preferably controlled to ensure a balance of properties including tensile strength compared to avoidance of slip-down during/after pre-leaching.

j. Uneven Bead—Bead Tear

Slippage on the former as per (h) and (i) above can then lead to problems with the beading stage. If the glove length is not long enough due to those factors, then there may be insufficient glove cuff length to allow for complete beading to occur—leaving a glove with either an incomplete bead, or no bead at all, which may appear as an apparent tear in the bead area. The difficulty of bead formation is due to the slippage of the wet gel (film). Accordingly, the surface roughness is preferably controlled to ensure a balance of properties including tensile strength on the one hand, and low defect rate due to imperfect beading.

k. Auto Stripping

In commercial glove manufacturing, for cost and quality control reasons, it is important for gloves to be capable of being stripped using conventional auto-stripping equipment with reasonably high stripping efficiency (i.e. rate of gloves successfully stripped by machine, without damage). The bead is used by the auto stripping equipment to allow glove removal from the former. If the bead is incomplete, this has a flow-on effect on auto-stripping—resulting in miss-stripping of the glove, and/or tearing of the glove during stripping. Other glove qualities (e.g. areas of weakness which lead to tears during stripping) may also have an impact on this stage of the process. Accordingly, account needs to be taken of the impact that the former surface roughness and other factors have on the stripping stage of the production process. The inventors have found that controlling the former surface roughness allows for auto-stripping to be achieved at a sufficiently high level of stripping efficiency, without overly compromising tensile strength for the low thickness gloves. Stripping efficiency can be at least 90%, at least 95% or at least 98%.

l. Rubber Residue on the Former

Severe adhesion of the glove to the former can also result in improper stripping, and this can lead to residual glove material/rubber residue remaining on the former. This can be a particular problem in the formation of ultra-thin-film gloves, due to the lower film thickness and cohesiveness of the film, leading to a high degree of rubber residue remaining. This was found to be a significant problem when attempting to make ultra-thin gloves on conventional formers. By changing the roughness of the former (compared to a conventional former), this problem was found to be significantly reduced.

m. Crotch Hole

Crotch hole, when present, is a serious defect and an indication of the film quality in the crotch (between finger) area. Crotch hole is an indication that the film in that zone is weak and this can result in premature failure of the glove. The inventors found from the data collected on the trial formers that crotch hole was nil in the V5 former.

n. Overall Analysis of Glove Product Qualities/Production Performance

The applicant compared the results achieve in the various tests and developed a table to illustrate the consolidated results, set out below.

In addition, in the above consolidated results table, "HP" refers to holes at the palm, "HCF" refers to holes at the cuff, "HCR" refers to holes at the finger crotch, and "HF" refers to holes at the fingertip area, all of which are as defined previously. In the "HP" and "HCF" evaluations, S/S 360 (Former Type V4) produced the most preferred and commercially viable results. In the "HCR" evaluation, S/S 540 (Former Type V5) produced the most preferred and commercially viable result. In the "HF" evaluation, S/S 540 (Former Type V5) and S/S 900 (Former Type V6) produced the most preferred and commercially viable result.

| S/S | Former Type | Former Surface 0-5 | Glove Shining 0-5 | Coagulant Pickup (Even/Uneven) | Latex Pickup (Even/Uneven) | Slip down (Gelling Stage) YES/NO | Slip down (Leaching Stage) YES/NO | Bead Uneven/Tear YES/NO | Auto stripping Station Observation |
|---|---|---|---|---|---|---|---|---|---|
| 360 | V4  | 0    | 0    | Even   | Even | No | No | No  | Easy Strip   |
| 540 | V5  | 0    | 0    | Even   | Even | No | No | No  | Easy Strip   |
| 900 | V6  | 2~3* | 2~3* | Even   | Even | No | No | No  | Easy Strip   |
| 540 | V7  | 1~2* | 1~2* | Even   | Even | No | No | No  | Easy Strip   |
| 900 | V8  | 3~4* | 3*   | Uneven | Even | No | No | Yes | Missed Strip |
| 480 | V9  | 1~2* | 1~2* | Uneven | Even | No | No | Yes | Missed Strip |
| 900 | V10 | 4~5* | 4~5* | Uneven | Even | No | Yes| Yes | Missed Strip |
| 900 | V11 | 2*   | 2*   | Even   | Even | No | No | No  | Easy Strip   |
| 900 | V12 | 5*   | 5*   | Uneven | Even | No | Yes| Yes | Missed Strip |

| S/S | Cuff Tear DPM | Rubber Residue DPM | Powder Mark DPM | Pin Holes DPM | Tensile Mpa | HP | HCF | HCR | HF |
|---|---|---|---|---|---|---|---|---|---|
| 360 | 55000*  | 0     | 11111* | 11000  | 35 | 2700   | 0      | 5000   | 2700 |
| 540 | 46000*  | 0     | 1852   | 26000* | 26*| 13000* | 11000* | 0      | 2000 |
| 900 | 56000*  | 0     | 12222* | 13000  | 31 | 5000   | 4000   | 3000   | 0    |
| 540 | 48000*  | 0     | 5556   | 42000* | 27*| 24000* | 3700   | 13000* | 1800 |
| 900 | 72000*  | 1000* | 6667   | 12000  | 39 | 1000   | 0      | 7000   | 4000 |
| 480 | 35000   | 0     | 6250   | 31000* | 37 | 8000   | 2000   | 18750* | 2000 |
| 900 | 90000*  | 0     | 0      | 5000   | 29 | 1000   | 1000   | 3000   | 0    |
| 900 | 37000   | 3000* | 1111   | 15000  | 26*| 3000   | 1000   | 9000   | 2000 |
| 900 | 133000* | 0     | 0      | 5000   | 48 | 0      | 0      | 3000   | 2000 |

In the above consolidated results table, the following abbreviations are used:

S/S—sample size;
0—not shiny;
1—low level of shine;
2—very mild shining;
3—mild shining;
4—obvious shine;
5—very shiny.

As shown in the above consolidated results table, in the "cuff tear" evaluation, S/S 900 (Former Type V8), S/S 900 (Former Type V10), and S/S 900 (Former Type V12) exhibited the highest three DPM values, which are not preferred. In the "powder mark" evaluation, S/S 540 (Former Type V5), S/S 900 (Former Type V10), S/S 900 (Former Type V11), and S/S 900 (Former Type 12) exhibited lowest DPM values, which are preferred. In the "pin holes" evaluation, S/S 360 (Former Type V4), S/S 900 (Former Type V10), and S/S 900 (Former Type V12) exhibited the lowest DPM values, which are preferred. In the "tensile strength" evaluation, S/S 900 (Former Type V8), S/S 480 (Former Type V9), and S/S 900 (Former Type V12) exhibited the highest tensile values, which are preferred.

Other consolidated test results are as follows:

|  | Average total DPM V4-V12 |
|---|---|
| Barrier Defects | |
| Cuff Tear    | 57300 |
| Hole Crotch  | 7275  |
| Hole Palm    | 6970  |
| Hole Cuff    | 4270  |
| Hole Finger  | 2550  |
| Visual Defects | |
| Powder Mark     | 5000 |
| Rubber Residue  | 500  |

Top 3 Highest Figures for Barrier and Visual Defects

|  | Barrier Defects | | |
|---|---|---|---|
|  | 1 | 2 | 3 |
| Cuff Tear | V12 | V10 | V8 |
|  | 133000 | 90000 | 72000 |

-continued

| | | | |
|---|---|---|---|
| Hole Crotch | V9 18000 | V7 13000 | V11 9000 |
| Hole Palm | V7 24000 | V5 13000 | V9 8000 |
| Hole Cuff | V5 11000 | V6 4000 | V7 3700 |
| Hole Finger | V8 4000 | V4 2700 | V5 2000 |

| | Visual Defects | | |
|---|---|---|---|
| | 1 | 2 | 3 |
| Powder Mark | V6 12000 | V4 11000 | V8 6000 |
| Rubber Residue | V11 3000 | V8 1000 | Others 0 |

"Cuff tear" refers to tearing at the cuff due to weakness during machine stripping.

The individual defect levels (barrier and visual) for each of the formers V4-V12 are as indicated in the tables below:

| Defects | V4 DPM | V5 DPM | V6 DPM | V7 DPM | V8 DPM | V9 DPM | V10 DPM | V11 DPM | V12 DPM |
|---|---|---|---|---|---|---|---|---|---|
| TEAR CF | 55556 | 46296 | 56667 | 48148 | 72222 | 35417 | 90000 | 37778 | 133333 |
| HOLE CR | 5556 | 0 | 3333 | 12963 | 6667 | 18750 | 3333 | 8889 | 3333 |
| HOLE P | 2778 | 12963 | 5556 | 24074 | 1111 | 8333 | 1111 | 3333 | 0 |
| TEAR P | 2778 | 5556 | 3333 | 0 | 2222 | 2083 | 4444 | 2222 | 17778 |
| HOLE F | 2778 | 1852 | 0 | 1852 | 4444 | 2083 | 0 | 2222 | 2222 |
| TOUCHING | 0 | 1852 | 1111 | 0 | 0 | 2083 | 2222 | 2222 | 0 |
| HOLE CF | 0 | 11111 | 4444 | 3704 | 0 | 2083 | 1111 | 1111 | 0 |
| KNOCKING | 0 | 0 | 0 | 0 | 0 | 0 | 0 | 0 | 0 |
| TEAR F | 0 | 0 | 0 | 0 | 0 | 0 | 0 | 0 | 0 |
| TEAR CR | 0 | 0 | 0 | 0 | 0 | 0 | 0 | 0 | 0 |
| BIG LUMPS | 0 | 0 | 0 | 0 | 0 | 0 | 0 | 0 | 0 |
| STN | 13889 | 5556 | 4444 | 11111 | 6667 | 37500 | 2222 | 10000 | 0 |
| POWDER MARK | 11111 | 1852 | 12222 | 5556 | 6667 | 6250 | 0 | 1111 | 0 |
| NRD < 1 MM | 8333 | 0 | 5556 | 24074 | 14444 | 20833 | 4444 | 6667 | 0 |
| ROLLED CUFF | 5556 | 0 | 0 | 0 | 2222 | 0 | 1111 | 0 | 2222 |
| DD | 2778 | 0 | 2222 | 7407 | 4444 | 0 | 2222 | 13333 | 0 |
| TACKY | 2778 | 7407 | 3333 | 3704 | 10000 | 0 | 20000 | 0 | 85556 |
| DISCOLOUR | 0 | 0 | 0 | 0 | 0 | 0 | 10000 | 0 | 0 |
| TS | 0 | 0 | 2222 | 5556 | 0 | 0 | 4444 | 1111 | 0 |
| WHITE SPOT | 0 | 1852 | 3333 | 0 | 0 | 0 | 0 | 0 | 0 |
| FM | 0 | 0 | 2222 | 0 | 0 | 0 | 0 | 3333 | 0 |
| NRD > 1 MM | 0 | 1852 | 0 | 0 | 0 | 0 | 0 | 1111 | 0 |
| STICKY | 0 | 0 | 0 | 0 | 0 | 0 | 35556 | 0 | 36667 |
| SHINING | 0 | 0 | 0 | 0 | 0 | 0 | 0 | 0 | 0 |
| RUBBER RESIDUE | 0 | 0 | 0 | 0 | 1111 | 0 | 0 | 3333 | 0 |
| BLISTER BEADING | 0 | 0 | 0 | 0 | 0 | 0 | 0 | 1111 | 0 |
| INCOMPLETE BEADING | 0 | 0 | 1111 | 0 | 0 | 0 | 0 | 0 | 1111 |
| ROLLED BEAD | 0 | 1852 | 0 | 0 | 0 | 0 | 0 | 0 | 0 |
| FORMER CRACK | 0 | 0 | 0 | 0 | 0 | 0 | 2222 | 1111 | 0 |
| OTHERS | 0 | 1852 | 0 | 0 | 0 | 0 | 0 | 0 | 0 |

The abbreviations used in the tables that have not previously been explained are as follows:
STN—Stain
DD—Double dipping
TS—Thin spot
FM—Flow Mark
NRD—Non removeable dirt
LM—Line mark
ICB—Incomplete beading Touching refers to the situation where the latex-coated former (with the latex in the gel or dried film form) touches something during the passage through the production stages (stations), causing the film to contain a small or large rupture. While care is taken to avoid external factors causing such touching defects, these can occur, and such gloves are considered to be defective. The stages or stations where this can occur include pre-leaching, beading, ovens (curing and/or drying ovens), surface treatment, post-leaching or otherwise.

Conclusions:

1. There are some positive and negative aspects that come from selecting formers with different surface roughness levels.

2. Some vital functions such as overall barrier qualities, powder mark, tensile strength and cleanliness of the former are better with formers such as V10 and V12.

3. Some functions such as shininess, coating of coagulant, bead formation and ease of stripping are better with formers V4, V7.

4. Ideally, a roughness ($S_z$) that gives the right balance of such properties should be selected.

5. In the consolidated results table, the most preferred and commercially viable attributes were marked with a triangle sign.

6. Following from point 5, it was observed that there were different preferences for the ultimate former surface roughness for different zones of the former/glove product. In the case of holes at the palm (HP), two types of former are most preferred—V4 and V11. For holes in the cuff (HCF), V4 is preferred (note that even though V8 and V12 provided the same results, they were considered to be less desired due to the uneven coagulant pick-up, uneven beading/tearing, miss-stripping and very high level of cuff tear). For holes in the finger crotch (HCR), V5 is preferred, and the achievement of a zero pin-hole defects level in that zone was very desirable. (As an aside, if the surface properties of V5 are present in a mould in the finger crotch zone only, the presence of a high palm hole defect rate is irrelevant.) Finally, for HF zone, V5 and V6 type former roughness is most preferred.

7. The idea was then developed of having a former with zones of different roughness tailored to the needs of that zone. It was anticipated, based on the results presented in this Example, that having zones of the former of different roughness values would give a product having a minimum number of the types of defects that are most problematic for that particular zone. Therefore, controlling the former roughness would assist in achieving an acceptably low defect rate for ultra-thin gloves.

8. A former denoted V13 was devised having the surface roughness in each of 4 zones (P, C, BF and F) that was selected based on the best results for that zone in the preliminary testing work on formers V4-V12. Former V13 was also designed with a cuff band area. An additional four sets of formers having similar properties in each zone to V13, but with one or two modifications, were also devised for comparison purposes. Former V17 contains the same surface properties in each zone as V13, but with a sharper V meeting point between the fingers, to improve strength in that area. The features of the formers are summarised as follows:

|  | Set A (V13) | Set B (V14) | Set C (V15) | Set D (V16) | V17 |
|---|---|---|---|---|---|
| Palm (P) zone (former V number) | V4 | V11 | V8 | V7 | V4 |
| Cuff (C) roughness (former V number) | V4 | V4 | V4 | V4 | V4 |
| Between Finger (BF) roughness (former V number) | V5 | V5 | V5 | V5 | New design - sharper "v" shape |
| Fingertip (F) roughness (former V number) | V6 | V5 | V6 | V5 | V6 |
| Cuff Band Zone | Added | Added | Added | Added | Added |

The former manufacturer was directed to produce the formers having the selected properties (selected from test formers V4 to V12), in each of the zones indicated in the table above. Four formers of each type were produced, and gloves were made on each of the types of the formers V13 to V17 as outlined below. The production of the formers required masking of zones of the former for performing the sand (ceramic compound) blasting/sand (ceramic compound) spraying operations to produce the target roughness properties for each zone separately, although where the zones were based on the same former properties (e.g. palm and cuff both V4), those zones were treated together. A cuff band area was also created in the formers, which contains etching creating a visible band area around the former with a higher surface roughness than the adjacent cuff zone.

In relation to former V17, this was produced in a manner consistent with former V13, but with a sharper crotch area to minimize the occurrence of weak spots in the finger crotch. The roughness of the zones was otherwise designed to be similar to the roughness of the zones of former V13.

The new formers were tested for their surface roughness in each zone. Gloves were produced on each of the formers using the latex formulation set out in the table below. Gloves with size medium of a nominal 2.2 grams in weight were produced, having a thickness of about 0.04 mm at the palm.

|  | 2.2 |
|---|---|
| Formulation | |
| NITRILE LATEX | 100 |
| KOH | 1.5 |
| SDBS | 0.2 |
| Colloidal Sulfur | 0.2 |
| ZDBC | 0.15 |
| ZnO | 0.45 |
| Anti oxidant | 0.1 |
| Sodium Aluminate | 0.3 |
| KOH | 0.6 |
| Glycerine | 0.3 |
| Coagulant | |
| Calcium Nitrate % | 8.5-10.5 |
| Calcium Stearate % (CaSt) | 2.0-3.0 |
| Particle size-CaSt (micron) | 8-15 |
| Terric % | 0.1 |
| Coagulant Dipping Profile | |
| In (secs.) | 6 |
| Dwell (secs.) | 4 |
| Out (secs.) | 6 |
| Latex TSC - Tank I | 12.5-13.5 |
| pH | 9.2-10.2 |
| Latex Dipping Profile | |
| In (secs.) | 5 |
| Dwell (secs.) | 6 |
| Out (secs.) | 7 |
| Latex TSC - Tank II | NA |
| pH | NA |
| Latex Dipping Profile | |
| In (secs.) | 5 |
| Dwell (secs.) | 6 |
| Out (secs.) | 7 |

The surface roughness $S_z$ of the former in the different zones, and of the gloves in the different zones, were measured using the Keyence VHX-6000 High Resolution Digital Microscope, operated in accordance with the operating instructions and in accordance with ISO 25178 (non-contact probe). The lens was the Z100 lens, and magnification was either 400× and 500×. The $S_z$ value measured by the instrument was recorded, and tabulated as follows:

|  | Former - Sz (μm) | | | | | Glove - Sz (μm) | | | |
|---|---|---|---|---|---|---|---|---|---|
|  |  |  |  |  | Cuff |  |  |  |  |
| Reference | Finger | Crotch | Palm | Cuff | Band | Finger | Crotch | Palm | Cuff |
| V13 | 69 | 34 | 33 | 28 | 55 | 50 | 32 | 31 | 33 |
| V14 | 49 | 29 | 27 | 28 | 39 | 38 | 17 | 26 | 17 |
| V15 | 66 | 29 | 23 | 20 | 35 | 44 | 13 | 23 | 20 |
| V16 | 78 | 27 | 24 | 23 | 40 | 54 | 16 | 19 | 17 |
| V17 | 71 | 33 | 33 | 23 | 53 | 52 | 31 | 30 | 32 |

Note that the cuff band is beaded, so the surface roughness of that zone is not measured in the glove product.

Gloves were made in a trial, commercial scale, production run with 4 of the V13 formers over a 21 day period, producing 2016 gloves. Each of the gloves was tested and found to have zero pinhole defects, in all glove zones. This was a remarkable result for the ultra-thin film thickness gloves. The data is set out below:

| Former Type | Date | HOLE (CUFF) Total Defects | DPM | HOLE (CROTCH) Total Defects | DPM | HOLE (PALM) Total Defects | DPM | HOLE (FINGER) Total Defects | DPM |
|---|---|---|---|---|---|---|---|---|---|
| V13 | 11 May 2018 | 0 | 0 | 0 | 0 | 0 | 0 | 0 | 0 |
| V13 | 12 May 2018 | 0 | 0 | 0 | 0 | 0 | 0 | 0 | 0 |
| V13 | 13 May 2018 | 0 | 0 | 0 | 0 | 0 | 0 | 0 | 0 |
| V13 | 14 May 2018 | 0 | 0 | 0 | 0 | 0 | 0 | 0 | 0 |
| V13 | 15 May 2018 | 0 | 0 | 0 | 0 | 0 | 0 | 0 | 0 |
| V13 | 16 May 2018 | 0 | 0 | 0 | 0 | 0 | 0 | 0 | 0 |
| V13 | 17 May 2019 | 0 | 0 | 0 | 0 | 0 | 0 | 0 | 0 |
| V13 | 18 May 2018 | 0 | 0 | 0 | 0 | 0 | 0 | 0 | 0 |
| V13 | 19 May 2018 | 0 | 0 | 0 | 0 | 0 | 0 | 0 | 0 |
| V13 | 20 May 2018 | 0 | 0 | 0 | 0 | 0 | 0 | 0 | 0 |
| V13 | 21 May 2018 | 0 | 0 | 0 | 0 | 0 | 0 | 0 | 0 |
| V13 | 22 May 2018 | 0 | 0 | 0 | 0 | 0 | 0 | 0 | 0 |
| V13 | 23 May 2018 | 0 | 0 | 0 | 0 | 0 | 0 | 0 | 0 |
| V13 | 24 May 2018 | 0 | 0 | 0 | 0 | 0 | 0 | 0 | 0 |
| V13 | 25 May 2018 | 0 | 0 | 0 | 0 | 0 | 0 | 0 | 0 |
| V13 | 26 May 2018 | 0 | 0 | 0 | 0 | 0 | 0 | 0 | 0 |
| V13 | 27 May 2018 | 0 | 0 | 0 | 0 | 0 | 0 | 0 | 0 |
| V13 | 28 May 2018 | 0 | 0 | 0 | 0 | 0 | 0 | 0 | 0 |
| V13 | 29 May 2018 | 0 | 0 | 0 | 0 | 0 | 0 | 0 | 0 |
| V13 | 30 May 2018 | 0 | 0 | 0 | 0 | 0 | 0 | 0 | 0 |
| V13 | 31 May 2018 | 0 | 0 | 0 | 0 | 0 | 0 | 0 | 0 |

Measurements were also taken of the V13 former palm roughness at 4 spaced apart points, in a 2 cm×2 cm square arrangement, and on the V13 glove in a similar 2 cm×2 cm spaced arrangement. The measurements were as follows:

| Points | V13 Former | V13 Glove |
|---|---|---|
| 1 | 36.42 | 35.18 |
| 2 | 36.04 | 34.06 |
| 3 | 34.32 | 32.77 |
| 4 | 35.19 | 34.01 |
| Average (rounded) | 35 | 34 |

Various modifications may be made as compared to the Examples without departing from the spirit and scope of the invention, as is described in the following Items and Claims.

The invention claimed is:

1. A synthetic elastomeric glove comprising a cuff, a palm, and fingers, the glove having:
   (a) a thickness at the palm of less than 0.050 mm, and at least one of:
   (b) a modulus at 500% above 6.5 MPa; and
   (c) an elongation at break below 700%.

2. The synthetic elastomeric glove of claim 1, wherein the glove has a modulus at 500% above 6.5 MPa and an elongation at break below 700%.

3. The synthetic elastomeric glove of claim 1, wherein the glove has a palm thickness of between 0.010 mm and less than 0.050 mm.

4. The synthetic elastomeric glove of claim 1, wherein the glove has a cuff thickness of less than 0.050 mm.

5. The synthetic elastomeric glove of claim 4, wherein the glove has an average of the palm thickness and the cuff thickness of less than 0.050 mm.

6. The synthetic elastomeric glove of claim 1, wherein the glove has a finger thickness of 0.070 mm or less.

7. The synthetic elastomeric glove of claim 6, wherein the finger thickness is between 0.015 mm and 0.060 mm.

8. The synthetic elastomeric glove of claim 1, wherein the glove has an average thickness of less than 0.050 mm, based on the average of the palm, cuff and finger thicknesses.

9. The synthetic elastomeric glove of claim 1, wherein the glove has weight of not more than 2.7 grams (or not more than 2.4 grams) for a glove length of 200 to 270 mm, or a weight of not more than 3.34 g (or not more than 2.8 grams) for a glove length of 270 to 330 mm.

10. The synthetic elastomeric glove of claim 1, wherein the glove has a weight of not more than 2.2 grams for a glove length of 200 to 270 mm.

11. The synthetic elastomeric glove of claim 1, wherein the glove comprises the cured product of a synthetic latex composition, the synthetic latex composition comprising a synthetic polymer and a cross-linking agent.

12. The synthetic elastomeric glove of claim 11, wherein the cross-linking agent comprises a solubilised trivalent metal compound.

13. The synthetic elastomeric glove of claim 11, wherein the cross-linking agent comprises a cross-linking composition, the cross-linking composition comprising an aqueous solution of a multimetal oxide of a multivalent metal, a multivalent metal hydroxide or a multivalent metal salt, producing an aqueous solution of negatively charged multivalent metal complex ions having a pH of at least 9.0.

14. The synthetic elastomeric glove of claim 13, wherein the multimetal oxide of the multivalent metal, the multivalent metal hydroxide or the multivalent metal salt is present in the synthetic latex composition in an amount of 0.3 phr or less.

15. The synthetic elastomeric glove of claim 12, wherein the synthetic latex composition further comprises sulphur, a sulphur donor, and a divalent metal oxide as secondary cross-linking agents.

16. The synthetic elastomeric glove of claim 11, wherein the synthetic polymer is selected from nitrile rubber, polyurethane, polyisoprene, polychloroprene, acrylic polymers, polybutadienes, and copolymers and modified forms thereof.

17. The synthetic elastomeric glove of claim 16, wherein the synthetic polymer comprises a carboxylated nitrile butadiene rubber.

18. The synthetic elastomeric glove of claim 1, which has a palm surface roughness ($S_z$) of between 26 µm and 41 µm.

19. A synthetic elastomeric glove with:
(a) a thickness at the palm of less than 0.05 mm;
(b) a modulus at 500% above 6.5 MPa; and/or
(c) an elongation at break below 700%,
comprising synthetic polymer and a cross-linking agent, wherein the cross-linking agent comprises solubilised trivalent metal compound having a pH of at least 9.

20. A batch of synthetic elastomeric gloves comprising a plurality of synthetic elastomeric gloves as claimed in claim 1, the batch having a defect maximum less than 4.0 AQL as determined in accordance with ISO 2859.

21. The batch of synthetic elastomeric gloves of claim 20, wherein the gloves of the batch have been produced using a stripping machine with a stripping efficiency of at least 90%.

22. A method of manufacturing the synthetic elastomeric glove of claim 1, comprising:
dipping a glove-shaped former into an elastomeric film-forming composition; and
curing the elastomeric film-forming composition on the former so as to produce the synthetic elastomeric glove.

23. The method of claim 22, wherein the glove-shaped former comprises (i) a palm zone, (ii) a cuff zone, (iii) between finger zones and (iv) finger zones, wherein:
the surface roughness ($S_z$) of the palm zone of the former is between 28 and 42 µm; and/or
the cuff zone of the former includes a textured cuff band region.

24. The method of claim 22, comprising dipping the former into a coagulant composition prior to the step of dipping the glove-shaped former into the latex composition wherein the coagulant composition comprises a mould release agent with a particle size such that at least 95% of the particles (D95) are of a size of less than 15 µm.

25. The method of claim 22, wherein the elastomeric film-forming composition has a total solids content of less than 30%, such as less than 25%, less than 20%, or from about 3% to about 15%.

26. The method of claim 22, wherein the glove-shaped former is dipped into the elastomeric film-forming composition for a total time period of from about 1 to about 50 seconds.

27. The method of claim 22, wherein the conditions during the production of the glove are as follows:
the coagulant concentration is between 0.1 and 20% based on multivalent metal ion concentration;
the total time period for coagulant dipping is between 1 and 30 seconds, such as between 10 and 24 seconds;
the latex total solids content is less than 30%, such as less than 25%, less than 20% or about 1 to about 20%; and/or
the total time period of dipping into the elastomeric film-forming composition is between 1 and 30 seconds, such as between 15 and 24 seconds.

28. The method of claim 22, comprising producing a batch of said gloves, and stripping the gloves from the glove-shaped former using a stripping machine with a stripping efficiency of at least 90%.

29. The method of claim 22, comprising producing a batch of said gloves with a defect rate less than 4.0 AQL, as determined in accordance with ISO 2859.

30. A synthetic elastomeric finger cot with:
(a) a thickness of less than 0.05 mm;
(b) a modulus at 500% above 6.5 MPa; and/or
(c) an elongation at break below 700%.

31. A method of manufacturing the synthetic elastomeric finger cot of claim 30 comprising:
dipping a finger-shaped former into an elastomeric film-forming composition; and
curing the elastomeric film-forming composition on the former so as to produce the synthetic elastomeric finger cot.

32. A glove-shaped former comprising (i) a palm zone, (ii) a cuff zone, (iii) between finger zones and (iv) finger zones, wherein:
the surface roughness ($S_z$) of the palm zone of the former is between 28 and 42 µm; and/or
the cuff zone of the former includes a textured cuff band region.

* * * * *